United States Patent
Deneuvile

(10) Patent No.: US 9,810,666 B2
(45) Date of Patent: Nov. 7, 2017

(54) DEVICE AND METHOD FOR NONDESTRUCTIVE INSPECTION OF TUBULAR PRODUCTS, ESPECIALLY ON SITE

(71) Applicant: VALLOUREC TUBES FRANCE, Boulogne Billancourt (FR)

(72) Inventor: Francois Deneuvile, Beaurepaire sur Sambre (FR)

(73) Assignee: VALLOUREC TUBES FRANCE, Boulogne Billancourt (FR)

( * ) Notice: Subject to any disclaimer, the term of this patent is extended or adjusted under 35 U.S.C. 154(b) by 235 days.

(21) Appl. No.: 14/773,634

(22) PCT Filed: Mar. 19, 2014

(86) PCT No.: PCT/FR2014/050643
§ 371 (c)(1),
(2) Date: Sep. 8, 2015

(87) PCT Pub. No.: WO2014/147344
PCT Pub. Date: Sep. 25, 2014

(65) Prior Publication Data
US 2016/0025684 A1    Jan. 28, 2016

(30) Foreign Application Priority Data
Mar. 21, 2013  (FR) ...................... 13 52548

(51) Int. Cl.
*G01N 29/22* (2006.01)
*G01N 29/24* (2006.01)
(Continued)

(52) U.S. Cl.
CPC ......... *G01N 29/265* (2013.01); *G01N 29/225* (2013.01); *G01N 29/2456* (2013.01);
(Continued)

(58) Field of Classification Search
CPC ............. G01N 29/225; G01N 29/2456; G01N 29/262; G01N 29/265; G01N 2291/2634; G01N 2291/056; G01N 2291/106
(Continued)

(56) References Cited

U.S. PATENT DOCUMENTS

| | | |
|---|---|---|
| 2007/0227249 A1 | 10/2007 | Meier et al. |
| 2008/0314154 A1 | 12/2008 | Fetzer et al. |
| 2009/0316531 A1 | 12/2009 | Brignac |

FOREIGN PATENT DOCUMENTS

| | | |
|---|---|---|
| EP | 1 830 158 A1 | 9/2007 |
| EP | 2 138 837 A2 | 12/2009 |

OTHER PUBLICATIONS

International Search Report dated Jul. 9, 2014, in PCT/FR2014/050643 filed Mar. 19, 2014.

*Primary Examiner* — J M Saint Surin
(74) *Attorney, Agent, or Firm* — Oblon, McClelland, Maier & Neustadt, L.L.P.

(57) ABSTRACT

A device for inspection of a tubular piece includes a cart including plural elemental ultrasound transducers distributed along at least a first direction and a guide which cooperates with an exterior surface of the piece to position the cart such that the first direction essentially corresponds to a direction transverse to the tubular piece. A control electronics, connected to the electroacoustic transducers, includes a memory storing the timed excitation laws and a controller that applies in succession a respective timed excitation law to subsets of mutually adjacent elemental transducers along the first direction. The timed excitation laws are designed so that the elemental transducers of the respective subsets jointly produce incident beams of ultrasonic waves propagating along respective directions inclined relative to a direction normal to the exterior surface of the tubular piece.

24 Claims, 10 Drawing Sheets

(51) Int. Cl.
  *G01N 29/26*  (2006.01)
  *G01N 29/265*  (2006.01)
(52) U.S. Cl.
  CPC ..... *G01N 29/262* (2013.01); *G01N 2291/056* (2013.01); *G01N 2291/106* (2013.01); *G01N 2291/2634* (2013.01)
(58) Field of Classification Search
  USPC .......................................................... 73/622
  See application file for complete search history.

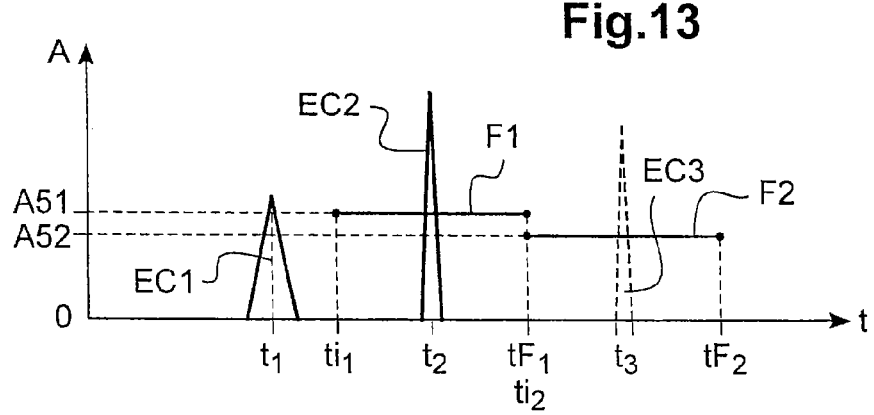
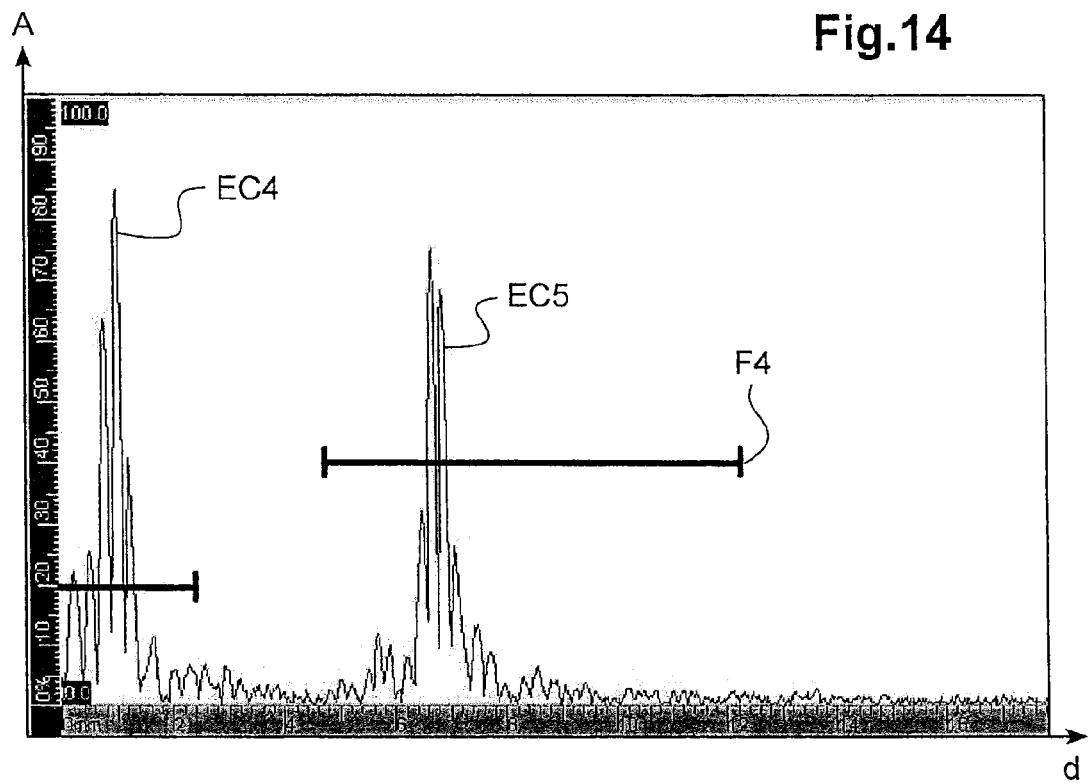

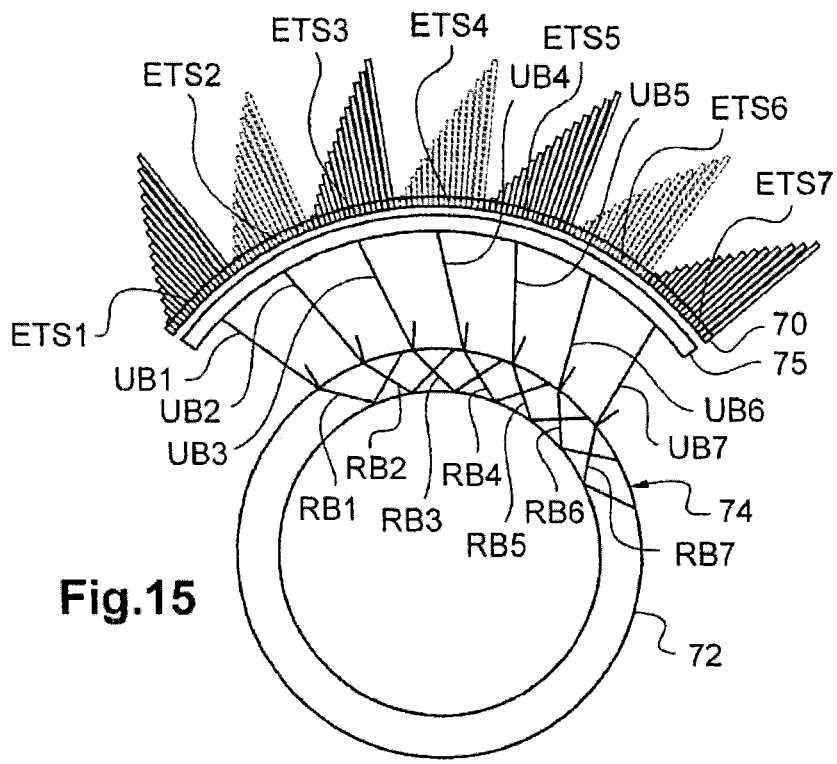
Fig.15
Fig.16
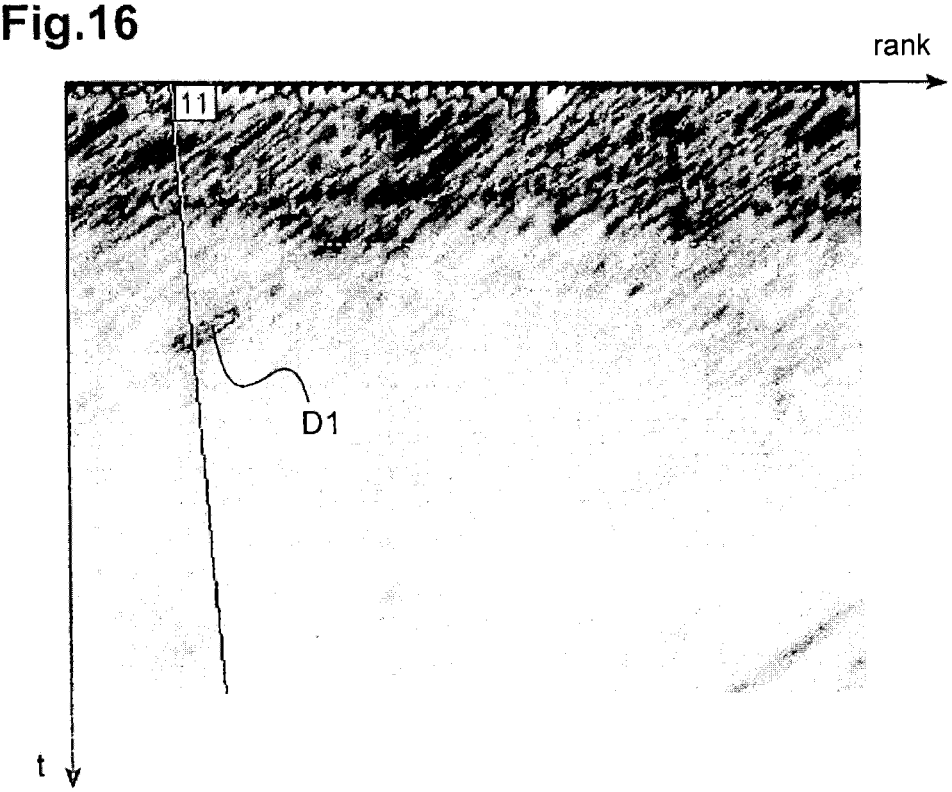

DEVICE AND METHOD FOR NONDESTRUCTIVE INSPECTION OF TUBULAR PRODUCTS, ESPECIALLY ON SITE

The invention deals with a device and a method for inspecting tubular steel pieces in nondestructive manner.

It is common to inspect such pieces after their fabrication, in particular at the production line itself, to detect the presence of flaws. The inspection is generally done with the aid of automatic inspection machines. Such machines in particular allow for a so-called "in line" inspection, where each piece produced is moved in its longitudinal direction with respect to an inspection machine. The machines in question can be of various type, in particular, ultrasound, Foucault current, or magnetic flux leakage.

The majority of the inspection machines used in production include one or more inspection probes in helicoidal movement with respect to the piece. Thus, the piece is scanned along its circumference and its length. Most often, the probes are arranged at the exterior of the piece, especially for reasons of time savings, ergonomics, and lower cost of the inspection machine. With such scans, one can obtain a true mapping of flaws in the inspected piece: one will have location data for each flaw in regard to the piece.

Customarily flaws may appear in the tubular piece and/or develop. In particular, this involves fatigue cracks or corrosion, corroded zones, or reduced thickness of the piece due to the formation of oxides on the inner surface, or also zones of reduced thickness due to erosion. It is necessary to detect such flaws in order to perform a diagnostics of the piece.

Frequently the tubular pieces are assembled one to another in order to form, on site, structures of relatively major size and/or complex geometry. For example, there might be drill columns, pipelines, power production plants, metallic structures, job site machinery and other heavy industrial vehicles, or gas cylinders.

It becomes necessary to inspect the tubular pieces of such structures in order to detect flaws occurring during use, and/or to monitor the evolution of flaws. Moreover, it may be desirable to check the tubular pieces after they have been assembled together, or at least prior to their use, in order to detect any flaws created during the assembly, and/or a negative evolution of preexisting flaws, due to this assembly. It is advisable to use a nondestructive method, and one which can be implemented without dismantling the structures in question.

Flaws, defects or deterioration on the exterior surface of the pieces can be detected by simple methods such as a visual examination, for example.

Flaws located on the interior surface of the product or in its thickness are much more difficult to find.

Unlike what occurs during production, once the pieces are installed on site it is practically impossible in the majority of cases to move them in relation to inspection probes by a helicoidal movement: the tubular pieces are generally fixed to each other and the footprint of the resulting structure, or its geometry, prevent any movement of the probe revolving around the pieces. This is especially the case whenever the tubular pieces are assembled in structures or panel shape, where the pieces are ranged alongside each other in a way very close together. This is the case in particular with heat exchangers, membrane tubes used in steam generators, or bent or arched portions of a conduit.

Inspection devices with internal probes, especially rotary ones, can be moved inside tubular pieces. These devices are rather impractical in use: one has to dismantle a portion of the tubular structure in order to insert them and/or provide access ports. Moreover, these devices have a tendency to get stuck inside the structures. It is then necessary to locate the devices and dismantle the structure until they are reached. Added to this is a longer inspection time, due to the need for a round trip in the structure and difficulties in guiding and coupling any device located inside the piece.

It becomes necessary to have inspection techniques on the exterior of tubular pieces on site, making possible a mapping of the structure, among other things. Techniques based on ultrasound are preferable, since these waves easily propagate in the pieces, even when the latter have a significant thickness, up to several hundred millimeters.

In structures having large constraints of footprint or complex geometry, one can move the portable ultrasound probes around the tubular pieces and along their length to cover the entire circumference of each piece of the structure. However, this results in a very long inspection time. It is necessary to provide a coupling medium between each ultrasound probe and the pieces being inspected, such as water or gel, for example.

Most often one uses a plexiglas waveguide, or one of other rigid material. This solution is ill suited to deteriorated surfaces, such as those one may find on pieces which have already been in operation.

Besides their slowness, the techniques which call for a circumferential displacement, especially a manual one, with respect to the pieces being inspected suffer from the practical difficulty of effectively covering the entire zone being inspected and enabling a correct traceability. It is hard to perform regular movements manually, with a constant sweep increment, simultaneously in the longitudinal direction of the pieces and along their circumference. As a result, it is impossible in practice to accomplish a mapping from the results of the inspection. In practice, the inspector is content to indicate crudely, for example by a marking, the doubtful zones. This complicates any traceability in the course of time.

From U.S. Pat. No. 7,975,549 B2 there is known a device for nondestructive inspection of pieces having an outer surface at least partly curved, especially a stringer for use in aeronautical manufacture. The apparatus comprises a housing with shape corresponding to the stringer, a mechanical guide to stabilize the apparatus with respect to the piece, an ultrasound translator, such as a piezoelectric one, comprising a plurality of elemental transducers regularly distributed along a circular arc, and a waveguide intercalated between the translator and the piece. The waveguide has a first surface of shape corresponding to the circular arc and a second surface, opposite the first one, whose curvature corresponds to that of the piece. Each elemental transducer emits ultrasound waves which propagate in a direction normal to the curved surface of the piece. The elemental transducers are activated one after the other, possibly in successive groups, so as to sweep an angle sector corresponding to the curved surface of the piece.

The stringer in question is an essentially solid piece and differs greatly from a tubular piece. The apparatus in question is only able to detect flaws at the same time situated in the curved portion of the stringer and oriented tangentially to this curvature. The apparatus is able to detect flaws in the thickness of the stringer, especially rolling defects of the type called laminar imperfections in the industry. However, it is not suited to the inspection of tubular pieces on site, for which one is most interested in finding flaws on the internal wall and/or flaws oriented essentially radially, such as fatigue cracks in particular.

From U.S. Pat. No. 7,984,650 B2 there is known a device whose mechanical structure basically resembles the device from U.S. Pat. No. 7,975,549 B2. A portable scanner of the kind used for a nondestructive inspection on site of pipes joined together by plates to form boiler panels comprises an ultrasound probe, a waveguide attached to the probe, and an encoder which provides a signal indicating a position of the probe with respect to the pipe being inspected. The shape of the waveguide needs to be adapted each time to the shape of the pipes of the panel. This document is silent on how to control the probe to inspect the pipes in question.

Furthermore, from U.S. Pat. No. 5,526,691 there is known a method of inspection on site of pipes of boiler panels, in particular as to the existence of corrosion cracks. The method uses two coils of the type known as EMAT: one of them emits a beam of ultrasonic shear waves with an angle of divergence determined each time as a function of the diameter of the pipes and their thickness, while the other coil receives the resulting ultrasonic waves, especially those relayed by any flaws present. Methods using EMAT coils are practically useless due to many drawbacks of this technology, such as a magnetization of the piece inspected, a strong magnetism which impairs the displacement of the coils relative to the pipe, and difficult diagnostics. This technology in particular does not enable a locating of the flaws, and especially a distinguishing of those located at the internal surface from those located at the outer surface. As a result, this technology is ill suited to producing a mapping of an installation constructed from tubular pieces.

From U.S. Pat. No. 5,549,004 there is known a device for on site inspection of pipes of boiler panels. The device in question proposes to detect reductions in thickness of the wall of the pipes. The device in question has a mechanical structure similar in principle to that of U.S. Pat. No. 7,975,549 B2. Document U.S. Pat. No. 5,549,004 calls for emitting beams of ultrasonic waves essentially perpendicular to the surface of the pipe being inspected, that is, generally without deflection. This allows, in theory at least, the inspecting of an angular portion between 60 and 70 degrees. According to the experience of the patent applicant, the dimension inspected and the nature of the flaws detected are for the most part insufficient.

From U.S. Pat. No. 7,516,664 there is known a method for inspection of a solid composite piece, in which one emits beams of ultrasonic waves deflected by means of a multi-element sensor. One transmits beams of longitudinal ultrasonic waves to the piece, having an inclination relative to the direction normal to the interface boundary of the piece between −10° and +10°. One thus produces a kind of scanning in a reduced range of inclination to select an inclination value allowing an optimal detection of porosities or laminar imperfections in a composite piece. The method in question is especially interesting for the inspection of pieces of imperfect geometry, particularly those nonsymmetrical and having a curvature difference between the intrados and the extrados. It does not allow a detecting of cracks on the interior and exterior surface, especially radial ones, at least not in satisfactory manner.

The patent applicant has tried to improve the existing situation. It has set itself the goal of a method and a device enabling a complete inspection on site of an installation based on tubular pieces, especially the searching for flaws located on the internal surface of the pieces, on the external surface, or near these surfaces. The method and the device should make it possible to distinguish the different flaws and to locate them in the cross section of the pieces and in their length. Moreover, the device and the method should allow the producing of a mapping of the installation, enabling among other things a monitoring of the appearance of flaws, and/or their evolution.

A device is proposed for the inspection of tubular pieces, of the type comprising at least one cart outfitted with a plurality of elemental transducers of the electroacoustic type, distributed along at least a first direction, and a guide able to cooperate with an exterior surface of a tubular piece being inspected so as to position the cart in a way such that said first direction essentially corresponds to a direction transverse to the tubular piece. A control electronics is connected to the electroacoustic transducers. The control electronics comprises memory storing one or more timed excitation laws and one or more controllers designed to apply in succession at least one respective timed excitation law to subsets of mutually adjacent elemental transducers along the first direction. At least some of the timed excitation laws are designed so that the elemental transducers of the respective subsets jointly produce incident beams of ultrasonic waves propagating along a respective direction which is inclined relative to a direction normal to the exterior surface of the tubular piece.

The proposed device makes it possible to scan at least one portion of a transverse section of a tubular piece and detect at the same time flaws near its interior surface, or emerging onto it, and flaws near its exterior surface, or emerging onto it. In particular, the proposed device enables a detection of flaws extending radially, such as cracks in particular. It is less costly to fabricate than an automated machine. Its inspection rate is compatible with the need for profitability, in particular in the case of pieces of complex shape. It is easy to manipulate and not bulky, so that it can easily be used on site, where the piece remains in the installed state.

There is also proposed a method for inspection of tubular pieces, in which a guide cooperates with an exterior surface of a tubular piece being inspected so as to position at least one cart outfitted with a plurality of elemental transducers of electroacoustic type such that the transducers are distributed along at least one transverse direction of the tubular piece, comprising at least one inspection stage involving a consecutive application of at least one timed excitation law to subsets of mutually adjacent elemental transducers along the first direction so that the elemental transducers of each respective subset jointly produce an incident beam of ultrasonic waves propagating along a direction inclined with respect to a direction normal to the exterior surface of the tubular piece.

Other characteristics and advantages of the invention shall appear upon perusal of the following description and the attached drawings, in which:

FIG. 1 schematically represents an installation based on tubular pieces;

FIG. 13 represents schematically a diagram of A-scan type, illustrating the amplitude of ultrasonic waves received as a function of the flight time of these waves.

FIG. 14 represents schematically a diagram of A-scan type, illustrating the amplitude of ultrasonic waves received as a function of the distance traveled by these waves;

FIG. 15 represents an inspection sequence with the aid of a multi-element sensor according to a first aspect of the invention;

FIG. 16 is a diagram of B-scan type illustrating the result of an inspection sequence according to the first aspect of the invention;

The attached drawings contain elements of a certain nature and can therefore serve not only to supplement the invention, but also assist in its definition, as the case may be.

Figure 1:
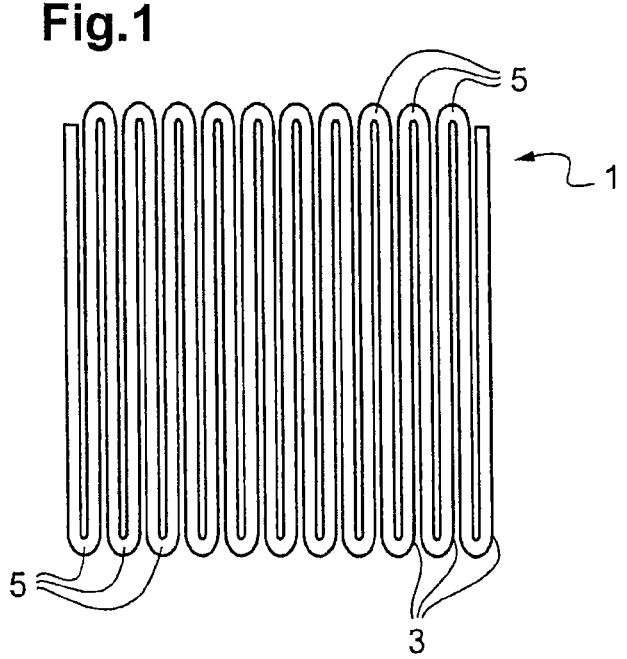

Reference is made to FIG. 1.

This shows an example of an installation based on tubular pieces in the form of a conduit 1 comprising a plurality of straight tubular segments 3, arranged in proximity to each other and interconnected by tubular elbows 5. The conduit 1 extends generally in a plane. The conduit 1 can be seen as making up a panel of tubular pieces, for example to be used as a heat exchanger between a fluid circulating inside the tubular pieces and a heat source situated outside these pieces, on at least one side of the panel.

The conduit 1 needs to be inspected. Each segment 3 needs to be inspected for flaws in its wall, especially cracks, in particular radial ones, whether these flaws are located on the internal surface of the segment 3, on its external surface, or near one or the other of these surfaces. The inspection should be done along the entire length of each segment 3 and cover a part of its transverse section on the order of half the circumference. In other words, it is necessary to check at least one surface of the panel formed by the conduit 1, typically the one situated on the side with the heat source in the case of a heat exchanger.

Due to the rather slight gap separating the two segments 3 from each other, it is practically impossible to inspect each segment 3 with the aid of a device moving transversely and/or pivoting around the segment 3. Furthermore, the segments 3 might be joined to each other.

On the other hand, such a technique would be too slow to be placed in industrial use.

Figure 2:
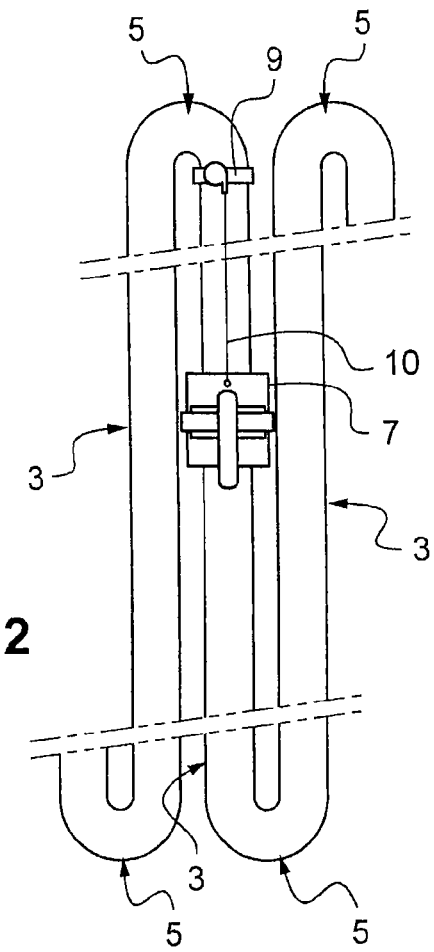
FIG. 2 represents a front view of an inspection device for tubular pieces, in working position on a part of the installation of FIG. 1.

Reference is made to FIG. 2.

This shows an inspection device, especially for the installation of FIG. 1. The inspection device comprises a portable cart 7 resting against the exterior surface of a tubular piece being inspected, here, a segment 3. The cart 7 can be moved along a longitudinal direction of the segment 3, here, manually. As a variant, the cart 7 can be motorized, at least to assist the operator in this movement.

Here, the inspection device furthermore comprises a position encoder connected to the cart 7 and putting out data which can be made to correspond to a position of the cart 7 with respect to the straight segment 3, at least along the longitudinal direction of this segment.

Here, the position encoder takes the form of a wire sensor 9, attached to the segment 3, near one of its lengthwise ends. One end of a wire 10 is attached to the cart 7 while the other end is attached to the sensor 9. The displacement of the cart 7 causes the wire 10 to roll up or unroll, depending on the direction of movement of the cart 7. A position datum can be derived from the wire length unrolled and/or rolled up, the number of turns performed by the reel, and/or the number of pulses corresponding to an angular pivoting of the reel.

In a variant, the position encoder can take the form of different embodiments, including a device mounted on the cart 7. For example, the position encoder can be of mechanical, linear or rotary, electromagnetic, optical type, or also take the form of an accelerometer. The choice of the type of encoder may depend on the geometry of the installation, at least at the zone being inspected, and/or of the elemental pieces of which it is composed. For example, to inspect a curved tubular portion of an installation, such as an elbow 5 of the installation 1, it is preferable to use a mechanical encoder.

Figure 3:
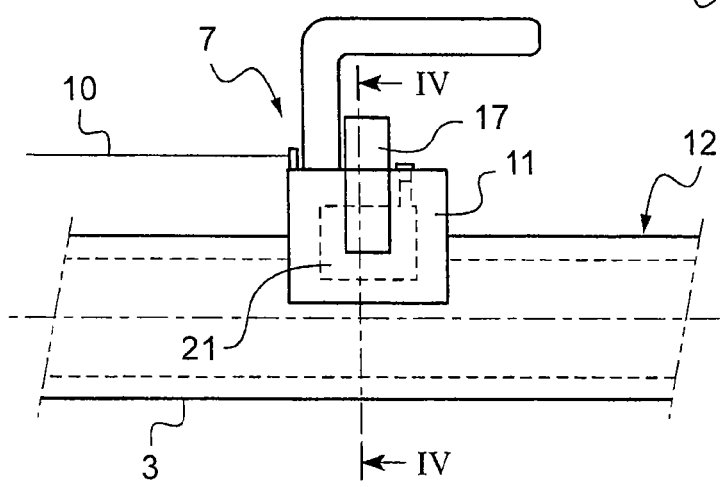
FIG. 3 represents the device of FIG. 2 in side view.
Figure 4:
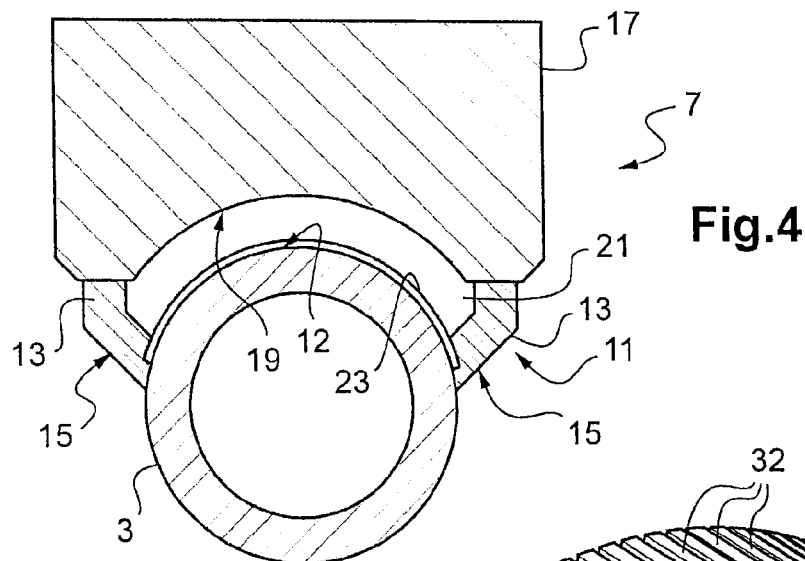
FIG. 4 represents the device of FIG. 3 in section along a line IV-IV.

Reference is made to FIGS. 3 and 4.

The cart 7 comprises a support 11 having a first face bearing against the exterior surface 12 of the segment 3 and with a shape corresponding to at least part of the profile of the segment 3.

Here, the support 11 is realized in the form of a profile of general U shape, whose arms 13 will be positioned on either side of the segment 3, across it. Each of the arms 13 terminates in a section 15 directed toward the inside of the U and which helps in holding the support 11 in position with respect to the segment 3.

The first face of the support 11 is shaped as a guide able to cooperate with the exterior surface of the segment 3 being inspected in order to position the cart 7 with respect to the segment 3. This first face also acts to guide the cart 7 in translation with respect to the segment 3, along its longitudinal direction. In other words, the first face of the support 11 can be seen as being a guiding/positioning face of the cart 7 with respect to the segment 3.

The cart 7 furthermore comprises an ultrasound translator 17 mounted on the support 11, at a second face of the latter, opposite the first face.

The ultrasound translator 17 has an active face, oriented toward the guide face of the cart 7, for the emitting and receiving of ultrasonic waves. The active face comprises an emitting/receiving surface 19 on which is regularly distributed a plurality of elemental transducers, of electroacoustic type, along a first direction, perpendicular to the arms 13 of the support 11. When the cart 7 is in position with respect to the straight segment 3 by means of the positioning guide, this first direction corresponds to a transverse direction of this straight segment 3.

Each elemental transducer can operate independently of the others. In particular, each elemental transducer can be excited to emit ultrasonic waves while responding to the reception of waves of this type by putting out an electric signal. Each elemental transducer is capable of operating as an emitter/receiver.

The surface of emission/reception 19 extends essentially between the arms 13 of the support 11.

Here, the surface of emission/reception 19 is curved. It has a shape corresponding to the profile of the segment 3, at least for a portion of this comprised between the arms 13 of the support 11. In other words, the surface of emission/reception 19 is conformed so as to follow, at constant distance when the cart 7 is in position, the portion in question of the profile of the segment 3. In the particular case illustrated in FIG. 4, the surface of emission/reception 19 is conformed as a portion of a round cylinder section, which corresponds to the circular profile of the segments 3. The surface of emission/reception 19 and the circular profile of the segments 3 are mutually concentric.

Here, the distance separating the surface of emission/reception 19 from the external surface 12 of the segment 3 is around 14.5 millimeters. The segment 3 has a radius of 25.5 millimeters whereas the surface of emission/reception 19 has a radius of curvature of 40 millimeters.

The surface of emission/reception 19 extends here for an angular portion of around 110°. Consequently, neither the translator 17 nor the support will abut against the segments 3 adjacent to the segment 3 on which the cart 7 is positioned. In this configuration, the translator 17 is of "semi-encircling" type. The elemental transducers are regularly distributed, in an angular manner, opposite a portion of the exterior surface 12 of the segment 3 being inspected.

The angular extent of the portion of emission/reception 19 essentially depends on the gap left free between two adjacent segments 3. To maximize the zone of the segment 3 which can be inspected, it is preferable to have the surface of emission/reception 19 extend to the maximum.

The inspection device further comprises an acoustic coupling mechanism, integrated with the cart 7 and intercalated between the active face of the translator 13 and the exterior surface 12 of the straight segment 3. The coupling mechanism is active when the guide face of the support 11 is in contact with the segment 3, regardless of the longitudinal position of the support 11 with respect to the segment 3.

Here, the coupling mechanism comprises a box 21 filled with water and closed by a flexible membrane 23. The membrane 23 is part of the contact surface between the cart 7 and the segment 3. It matches the shape of the segment 3 on an angular portion of the latter corresponding to the active surface 19 of the translator 17. The membrane 23 is made from a material having a slight attenuation of the ultrasonic waves, and in which the speed of propagation of said waves is close to that of water, or the coupling medium as applicable. Thus, the presence of the membrane 23 has practically no influence on the calculation of the laws of delay applied to the elemental transducers, or on the refraction of the ultrasonic waves. The membrane 23 can be made of the material known as Aqualene.

The flexibility of the membrane 23 allows the device to adapt to a deteriorated state of the outer surface 12 of the segment 3. In addition, a coupling gel or water can be intercalated between the outer surface 12 and the membrane 23.

As a variant, the box 21 can have a free flow, that is, lacking a membrane 23. The water pressure should then be sufficiently high so that the space between the surface of emission/reception 19 and the outer surface 12 remains filled with water. Recuperation tanks and a water recycling circuit can be installed in such a case.

The box 21 can be replaced, at least in part, by a flexible flange of material with acoustic properties, adapted to the refraction of the ultrasonic waves in steel, for example, of a type similar to that of the membrane 23, or by a rigid flange made from a material of plexiglas type, for example.

Optionally, the support 11 can be outfitted with a supplemental guide to facilitate a movement of the cart 7 along the longitudinal direction of the segment 3. In particular, this supplemental guide is designed to cooperate with the positioning guide so that the cart 7 maintains its transverse position with respect to the segment 3 during the movement in question. Guide rollers can be mounted on the support 11, for example, on its arms 13.

As yet another option, the cart 7 can be outfitted with a tensioning mechanism able to flatten the membrane 23, the box 21 and/or the flange against the outer surface 12 of the segment 3. For example, one can use one or more compression springs.

The inspection device further comprises a control electronics, to which the translator 17 and the position encoder 9 are individually connected.

The control electronics is able to send excitation signals to each elemental transducer of the translator 17 for the emitting of ultrasonic waves.

Figure 5:
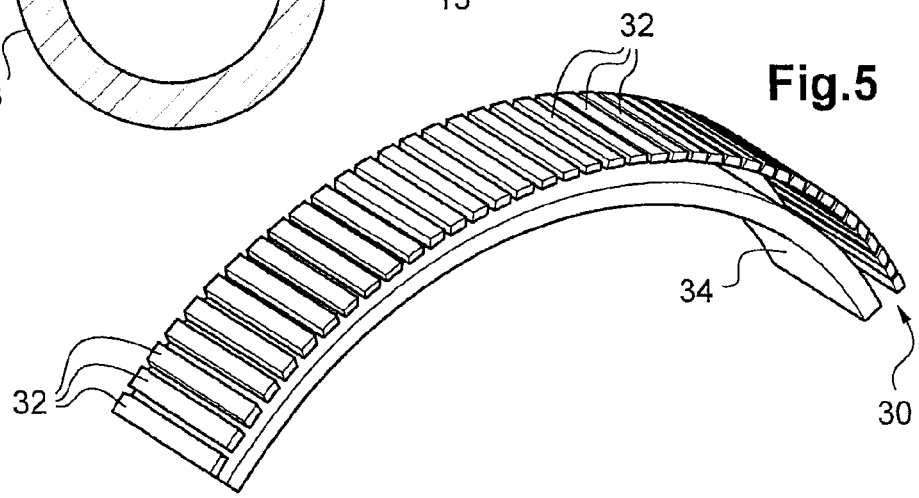
FIG. 5 represents a multi-element sensor of a first type, in perspective view.

Reference is made to FIG. 5.

This shows a multi-element sensor 30 of the kind used for example as a surface of emission/reception 19 in FIG. 4. The sensor 30 comprises a plurality of ultrasound transducers 32, for example, piezoelectric ones, similar to each other and distributed in a line on a curved surface. Each ultrasound transducer 32 is presented here in the form of a flat rectangular element. The ultrasound transducers 32 are mutually aligned along their width.

For example, the ultrasound transducers 32 here each have a width of 0.5 millimeters and are mutually spaced apart by 0.1 millimeters.

Here, the multi-element sensor comprises a protection strip 34, for example in the form of a resin layer of known type, familiar as epoxy resin.

Figure 6:
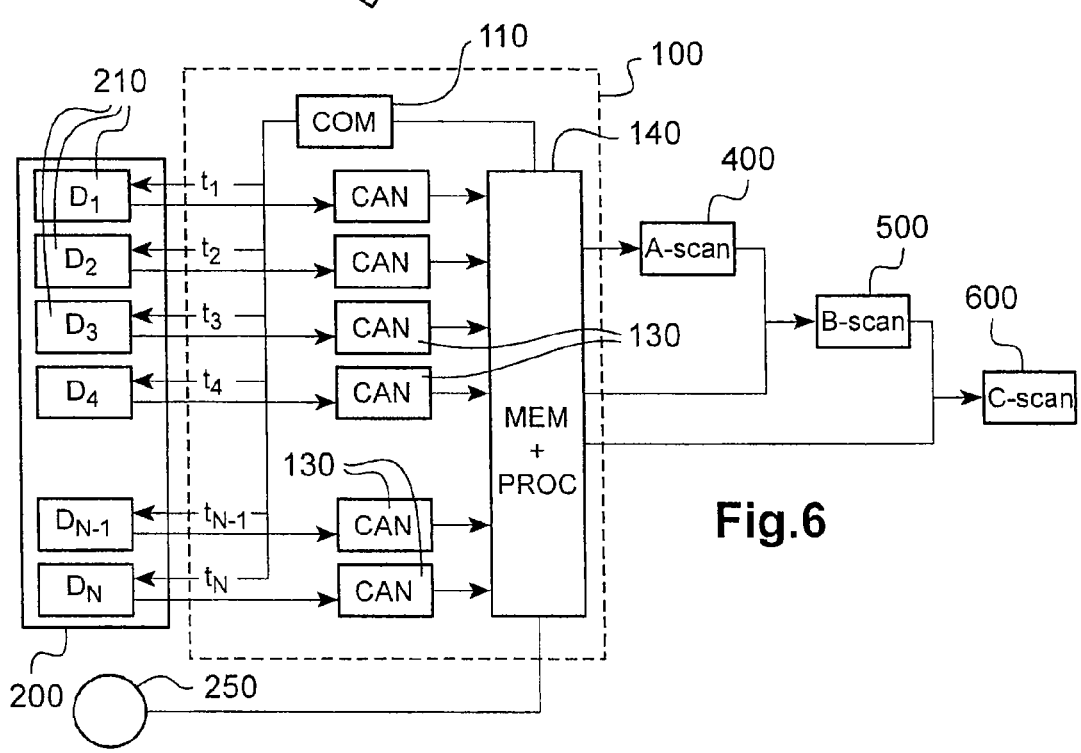
FIG. 6 represents a functional diagram of a control electronics for example to be used in the device of FIGS. 2 to 4.

Reference is made to FIG. 6.

This is a functional representation of a control electronics 100 designed for a multi-element ultrasound sensor 200, such as the sensor 30 of FIG. 5.

The sensor 200 comprises a plurality of elemental transducers 210, referenced as e1, e2, . . . , ei, . . . eN, where N represents the number of elemental transducers 210 of the sensor 200. In the functional diagram of FIG. 6, the N elemental transducers 210 are arranged in a line. In actuality, the transducers in an ultrasound sensor can be organized into a table, each one having an address number.

The elemental transducers 210 are able to function in emission/reception in the ultrasound sensor 200.

The electronics 100 comprises an emission pathway in the form of a control circuit 110 electrically connected to each of the transducers 210. The control circuit 110 is able to excite each transducer 210, that is, make it emit a pulsed wave at an ultrasound frequency between, for example, 1 and 15 MHz. The ultrasound frequency used depends in practice on the size of the flaws being looked for. For the application described here, a value on the order of 5 MHz is particularly suitable.

The electronics 100 furthermore comprises a processor 140 one output of which is connected to the control circuit 110. The processor 140 can activate the control circuit 110 to excite one or more elemental transducers 210.

The transducers 210 can be excited by groups, each with a phase offset or time delay in relation to a time origin common to the transducers of the group. In general, we designate as ti the time delay for the excitation of the transducer ei in relation to its time origin. Memory, for example memory associated with the processor 140, saves one or more timed excitation laws. The processor 140 can successively call up at least some of these laws for subsets of elemental transducers to have them be applied by the control circuit 110 in order to carry out what may be called an inspection sequence.

The processor 140 and the control circuit 110 thus act jointly in the manner of a controller which is able to apply in succession at least one respective timed excitation law to subsets of elemental transducers 210. The application of a timed excitation law to a subset of elemental transducers 210 results in the emitting of a beam of ultrasonic waves by the elemental transducers 210 in question. This emission can also be called a "shot" as a term of art.

The sensor 200 is both an emitter and a receiver. Ultrasonic waves can be received by the transducers 210. The electronics 100 comprises a plurality of analog/digital converters 130. The input of each converter 130 is connected to a respective transducer 210 while its output is connected to a respective input of the processor 140. The electric signals coming from the transducers 210 can thus be converted into digital signals and saved, for example, in the memory of the processor 140.

The memory saves the digital signals in association with data enabling an identification of a subset of transducers 210 to which the timed excitation law was applied.

The processor 140 is moreover programmed to phase the time signals saved in memory and corresponding to the transducers of the same group, among other things. More generally, the processor 140 is able to operate on the digital signals in memory, each time in regard to the same identification data, that is, the same subset of transducers 210. Thus, it acts as a processing module in the control electronics 100.

One input of the processor 140 can be connected to a pulse encoder 250, for example, the encoder 9 of FIG. 2.

The processor 140 can furthermore be programmed to add the signals corresponding to each shot of each group of transducers to generate an A-scan 400. In order to place the signals in phase, the delays used during the emission can be applied inversely in one particular embodiment, that is, the largest delay values are applied in reception mode to the signals received by the transducers that were excited with the smallest delay values.

In one advantageous development, a processing operation can involve the application of one or more delay laws different from those used in the emission mode, corresponding to different inclination values, to each signal received. A processing of this type is described, for example, in the international application filed in the name of the present applicant and published as number WO 2003/50527. Such a processing can improve the detection of certain flaws, in particular, those inclined with regard to the radial direction.

A processing of the data received makes it possible to generate B-scan 500 representations by building up the A-scans in the order of the consecutive groups used during a circumferential sweep. Finally, the C-scan 600 representations, or cartographies, can be reconstructed by building up the information of the B-scans correlated with the distance traveled during the movement of the device along the tubular pieces.

Figure 7:
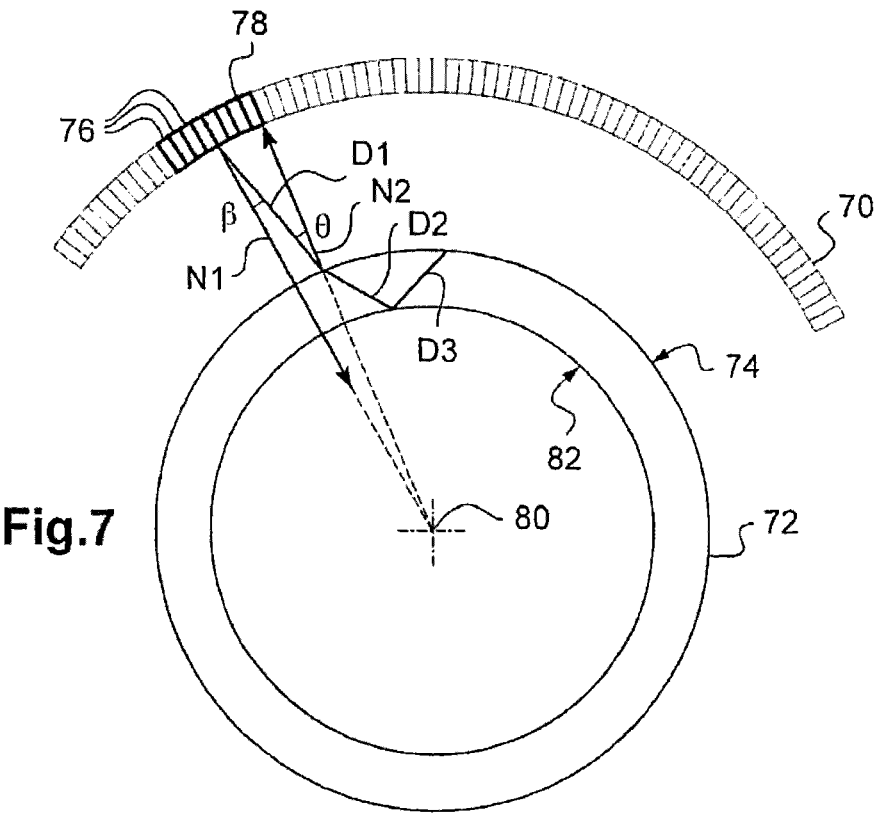
FIG. 7 represents an emission of ultrasonic waves from a multi-element sensor, in working position with respect to a piece being inspected.

Reference is made to FIG. 7.

It shows a multi-element sensor 70, similar to the sensor 30 of FIG. 5, in position with respect to a pipe 72, opposite a portion of an outer surface 74 of the latter.

A timed excitation law can be calculated in a way such that elemental transducers 76 of a subset 78 jointly produce a beam of ultrasonic waves. The emitted beam is represented by its direction of propagation D1 in FIG. 7.

In a transverse plane of the pipe 72, the direction D1 of the emitted beam is inclined by an angle of deflection $\beta$ with respect to a direction N1 normal to the surface of the sensor 70 near the outer surface 74, at least in an essentially median, or central position, of the group of transducers 78. The sensor 70 here is positioned with respect to the pipe 72 such that the normal direction N1 passes through the center 80 of the transverse section of the pipe 72.

The direction D1 is inclined by an angle of incidence $\theta$ with respect to a direction normal N2 to the outer surface 74 of the pipe 72, where the first direction D1 meets this outer surface 74.

The timed excitation law corresponds to the set of delay values by which each elemental transducer 76 of the subset 78 is excited in relation to a time origin which is common to the elemental transducers of the subset.

The formula of Annex A.1 indicates in general fashion the delay value $\Delta t_n$, expressed in seconds for example, to be applied to the elemental transducer 76 of rank n in the subset 78. In this formula:

The quantity $d_n$, expressed in meters for example, corresponds to the distance separating the first transducer of the subset from the transducer of rank n, considered from the center of one transducer to that of the other transducer. The distance $d_n$ can be calculated from the dimensions of the elemental transducers and the mutual spacing of the elemental transducers.

The angle $\beta$ corresponds to the angle of deflection in the coupling medium, that is, the inclination in the direction of propagation D1 of the beam with respect to the normal N1 to the plane of the central transducer. This angle can also be called the "angle of emission".

The quantity V corresponds to the speed of the ultrasonic waves in the coupling medium, for example, 1480 m/s in water.

The beams of ultrasonic waves emitted can have no focus, or at least have a focus point very far from the sensor 70 in relation to the distance separating the sensor 70 from the pipe 72. In this case, the flaws near the outer surface 74 of the pipe and those near the inner surface of the pipe 70 can be detected with the same sensitivity. As a variant, at least some of the beams emitted have a focal point near the pipe 72, for example, at its inner surface, its outer surface 74, or in the thickness of the pipe 72. One then gives preference to a detection of flaws in the corresponding zone of the pipe 72.

The formulas of Annexes A.3 and A.4 make it possible to calculate a value of the angle $\beta$ of inclination of the ultrasound beam with respect to the sensor as a function of a value of the angle of incidence $\theta$ to the outer surface 74 of the pipe 72.

In this formula:

The quantity $r_1$ corresponds to the outer radius of the pipe 72.

The quantity $r_2$ corresponds to the radius of curvature of the surface of emission/reception of the active face of the sensor 70.

Figure 8:
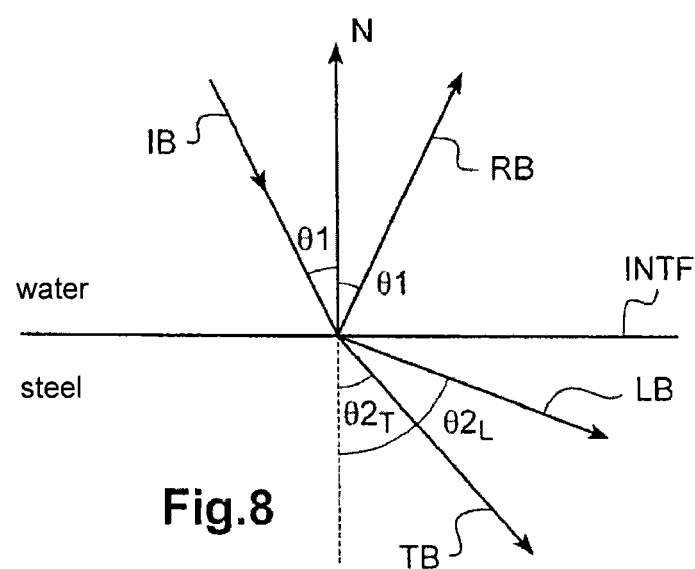
FIG. 8 represents the reflection and the refraction of ultrasonic waves on the surface of a piece being inspected.

Reference is made to FIG. 8.

At an interface IVF between the coupling medium and the steel, here, water and steel, such as the outer surface 12 of the piece of FIG. 4, an incident beam of longitudinal ultrasonic waves, represented here by its principal direction of propagation IB, having an angle of incidence $\theta 1$ not zero with respect to a direction N normal to the interface, is refracted into a beam of longitudinal ultrasonic waves which propagates in a principal direction LB inclined by an angle of refraction $\theta 2_L$ not zero with respect to the normal direction N, and a beam of transverse ultrasonic waves which propagates in a principal direction TB inclined by an angle of refraction $\theta 2_T$ not zero with respect to the normal direction N.

Moreover, the incident beam is partly reflected at the interface IVF into a beam of longitudinal ultrasonic waves which propagates in a principal direction RB inclined by an angle of reflection equal to the angle $\theta 1$ with respect to the direction N.

Starting from a value of the angle of incidence $\theta 1$, corresponding values of the angles of reflection and refraction can be calculated by using the formula of Annex A.2, where:

the value $V1_L$ corresponds to the speed of the longitudinal acoustic waves in water, or around 1480 m/s;

the value $V2_L$ corresponds to the speed of the longitudinal acoustic waves in steel, or around 5900 m/s;

the value $V2_T$ corresponds to the speed of the transverse acoustic waves in steel, or around 3230 m/s.

Figure 9:
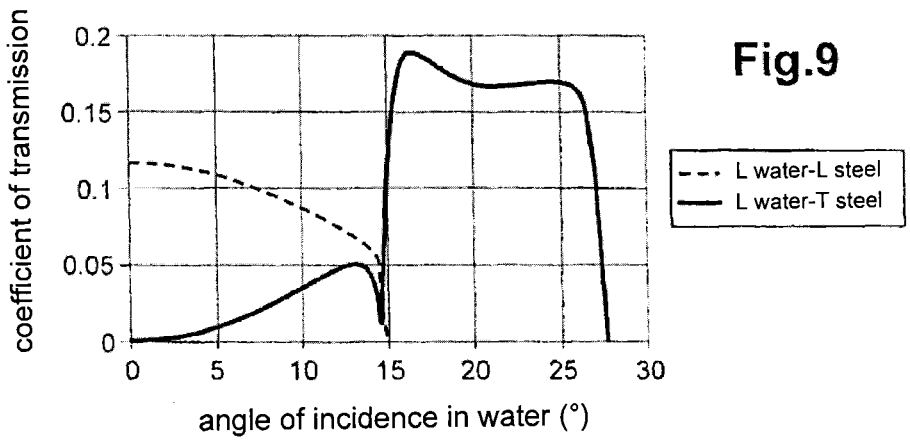
FIG. 9 represents an evolution of the refraction of ultrasonic waves in steel as a function of the angle of incidence.

Reference is made to FIG. 9

This shows a diagram illustrating the variation in the value of the coefficient of transmission (ordinate) of an incident beam of longitudinal ultrasonic waves propagating in water and being refracted, on the one hand, into a beam of longitudinal ultrasonic waves in steel (broken line) and, on the other hand, into a beam of transverse ultrasonic waves in steel (solid line), each time as a function of values of the angle of incidence (abscissa). The higher the value of the coefficient, the more sizeable the energy of the particular wave in the steel.

A wave with a sizeable energy improves the conditions of inspection. However, a lower energy can be compensated, in particular, by increasing the reception gain.

The diagram of FIG. 9 shows that:

for values of the angle of incidence between around 15° and around 27°, the refracted waves are only transverse;

the values of the coefficient of transmission in transverse waves corresponding to values of the angle of incidence between around 15° and around 27° are clearly greater than the largest values of the coefficient of transmission in longitudinal waves;

for values of the angle of incidence greater than around 27°, the coefficients of transmission in transverse waves and in longitudinal waves are practically zero. Only essentially surface waves are generated at the interface between water and steel. Such waves, generated on the outer surface of a tubular product, do not allow the detecting of either flaws at the inner surface of the tubular product or flaws oriented radially in the thickness of the product or on its outer surface.

It is advantageous, especially to simplify the interpretation of the control, to use for the inspection of tubular pieces values of the angle of incidence in water between around 15° and around 27°, which correspond to elevated values, greater than around 0.15, of the coefficient of transmission in transverse waves. This enables an inspection with a high energy level.

Values of the angle of incidence in water less than around 15°, for which the two types of wave, longitudinal and transverse, coexist in steel, are not excluded. The interpretation of the various rebounds of the two waves may prove to be more complex, however.

Figure 10:
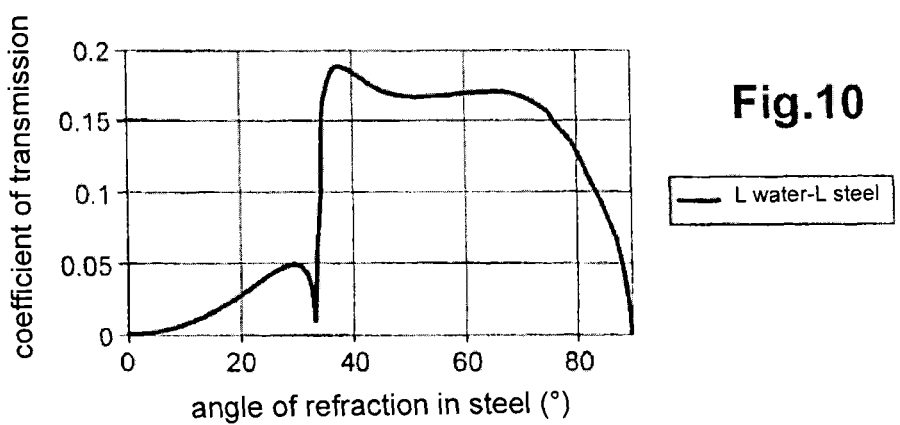
FIG. 10 is analogous to FIG. 9, for values of the angle of refraction.

Reference is made to FIG. 10.

This shows a diagram analogous to that of FIG. 9, where the variation of the value of the coefficient of transmission is indicated as a function of values of the angle of refraction, and only for the transverse waves. High values of the coefficient of transmission correspond to values of the angle of refraction in transverse waves between around 35° and around 80°.

Reference is made once again to FIG. 7.

Depending on the choice of the angle of incidence $\theta$, a beam of ultrasonic waves, especially transverse ones, is refracted in the thickness of the pipe 72, this beam being represented here by its direction of propagation D2. The latter arrives at the interior surface 82 of the pipe 72, the result being a reflected beam of ultrasonic waves, represented by its direction of propagation D3. This corresponds to what is called a "rebound" or "bounce" in the terms of the art. Even though not shown in FIG. 7, the beam propagating in the direction D3 is reflected at the outer surface 74 in another bounce and so forth.

Figure 11A:
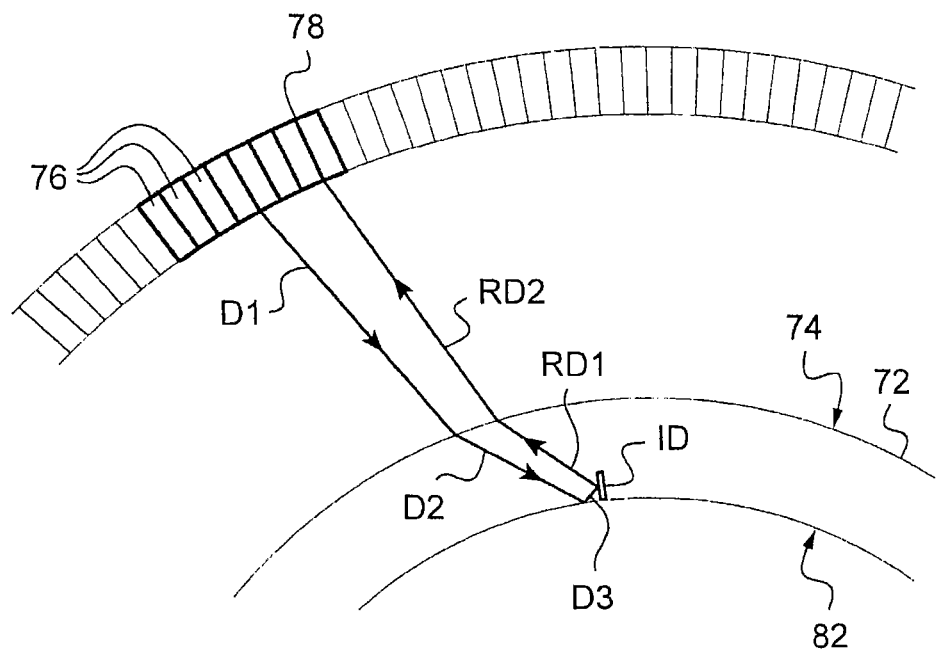
FIG. 11A represents the reflection of an ultrasonic wave by a flaw of a first type.

Reference is made to FIG. 11A.

In similar manner to what was described in connection with FIG. 7, the set 78 of elemental transducers 76 such as those of the multi-element translator 17 of FIG. 4 can emit toward the outer surface 74 of the tubular steel piece 72, such as the outer surface 12 of a segment 3, a beam of ultrasonic waves which is propagated in a coupling medium, such as water, in a first direction D1. The beam emitted is refracted at the outer surface 74 into a beam of ultrasonic waves which propagates generally in the second direction D2. The refracted beam is reflected at the steel/air interface formed by the inner surface 82 of the piece 72 into a beam propagating primarily in the third direction D3.

When this reflected beam encounters a surface of a flaw ID, here internal and radial, the latter reflects a beam of ultrasonic waves which propagates primarily in a first return direction RD1. At the interface formed by the outer surface 74 and the coupling medium, the reflected beam is refracted into a beam of ultrasonic waves propagating in a second return direction RD2. The latter may be picked up by elemental transducers 76 opposite the outer surface 74. In the case of a tubular piece and a flaw extending generally in radial manner, the reflected beam is primarily received by the transducers 76 of the subset 78 used for the emission.

In similar fashion, not represented in FIG. 11A, the refracted beam propagating in the second direction D2 could get reflected by an internal flaw without prior reflection at the inner surface 82 of the piece 72.

The refracted beam of ultrasonic waves propagating along D2 is suitable for the detecting of longitudinal flaws located at the inner surface 82 of the piece 72, or in its proximity Flaws having such a configuration include in particular corrosion or fatigue cracks.

Figure 11B:
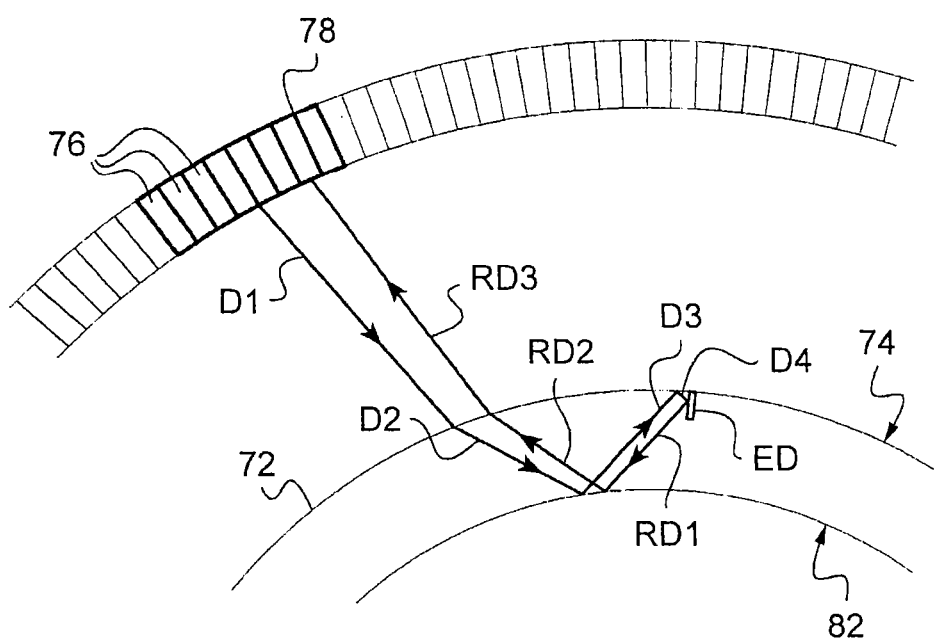
FIG. 11B represents the reflection of an ultrasonic wave by a flaw of a second type.

Reference is made to FIG. 11B.

This is similar to FIG. 11A, except that the refracted beam propagating in the direction D2 does not encounter any flaw until it reaches the internal surface 82 of the piece 72. It is reflected here into a beam propagating along the direction D3, and is itself reflected at the outer surface 74 of this piece 72 into a beam propagating along a fourth direction D4. This latter encounters a surface of a flaw ED, here external and radial, and is reflected by it into a beam propagating along the first return direction RD1, reflected by the internal surface 82 into a beam propagating along a second return direction RD2, which is refracted at the external surface 74 of the piece 72 into a beam propagating along a third return direction RD3. This latter is received by the elemental transducers 76. Due to the radial orientation of the flaw ED in the piece 72, the beam propagating along the third return direction RD3 is primarily received by elemental transducers 76 of the subset 78 used for the emission.

The beam along direction D2 is suitable to detecting longitudinal flaws located in the vicinity of the outer surface 74 of the piece 72, or close to it.

FIGS. 11A and 11B each show a principal trajectory of the beams of ultrasonic waves corresponding to the directions of propagation of working beams for detecting a flaw. In practice, secondary or ancillary beams can be generated by refraction or reflection each time a working beam encounters an interface of steel/coupling medium or steel/air. These secondary beams are not useful in the detecting of flaws in the piece 72, at least not directly. For this reason, and for purposes of simplicity, the trajectory of secondary beams has not been indicated in FIGS. 11A and 11B. For example, in FIG. 11B the beam propagating along the third direction D3 generates, at the steel/coupling medium interface, a beam of refracted ultrasonic waves (not shown) in the coupling medium, in addition to the beam of reflected waves propagating along the fourth direction D4. Unlike the beam propagating along the direction RD3, the beam of refracted waves in question is not received by the elemental transducers 76 of the emitting subset 78.

FIGS. 11A and 11B show that at least some of the ultrasound waves emerging from the piece 72, especially those resulting from a reflection by a radially oriented flaw, are received by the elemental transducers of the emitting subset, or at least some of them.

According to one embodiment of the inspection device, it comprises a processing electronics, or module, such as the processor 140 of the electronics 100 of FIG. 6, designed to process only the signals received by the elemental transducers of the subset which has emitted the incident beam. In other words, the processing electronics operates each time on digital representations of electric signals resulting from a reception of ultrasound waves by the elemental transducers of the subset to which a timed excitation law has just been applied. The time needed for the processing of the signals received is in this case reduced, and it remains consistent with a classical inspection cadence, while still enabling a detection of radial flaws.

According to a different embodiment, the processing electronics is designed to process the signals received at the set of elemental transducers of the sensor in response to the emitting of a beam of ultrasound waves by only one subset of these transducers. Among other things, the inspection device then makes it possible to detect flaws oriented in different manner in the piece, that is, not oriented in radial manner.

According to yet another embodiment, the processing electronics can be designed so as to process only signals received at one or more subsets of elemental transducers different from the emitting subset.

Figure 12:
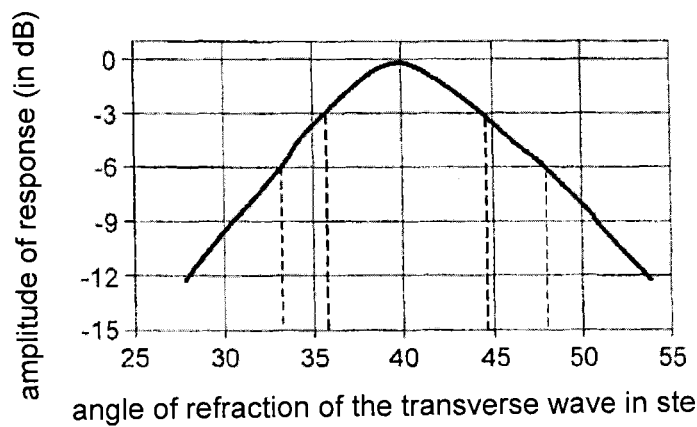
FIG. 12 represents an evolution of the amplitude of response of a flaw as a function of values of the angle of refraction in steel.

Reference is made to FIG. 12.

This shows a diagram indicating the amplitude of the echo (ordinate), or response, reflected by a typical flaw (close to the internal surface) as a function of the value of the angle of refraction of a beam of transverse ultrasonic waves in steel (abscissa).

The amplitude values correspond to the case of a tubular piece having an outer diameter of 51 millimeters and a thickness of 5 millimeters. The typical flaw takes the form of a nick in the wall of the piece extending along the length of the piece and radially to it. The nick emerges onto the internal surface of the piece and extends down to a depth of 0.5 millimeters.

The frequency of the ultrasound waves emitted is close to 5 Megahertz.

Values of the angle of refraction near 40° are optimal. In the case of water as the coupling medium, this corresponds to values of the angle of incidence near 17°. Values of the angle of refraction between around 33° and around 47° allow one to obtain an echo amplitude greater than −6 decibels. Values of the angle of refraction between around 37° and around 45° make it possible to obtain a relative echo amplitude greater than −3 decibels.

A refracted beam of transverse ultrasonic waves which is propagating along a direction inclined by around 40° with respect to the direction normal to the outer surface of the tubular piece being inspected is preferred in that it allows one to detect internal and external flaws and make best use of the energy of the ultrasound translator.

For simplicity, we have limited the diagram of FIG. 12 to values of the angle of refraction between around 26° and around 54°. Values of the angle of refraction less than 26° or greater than 54° can be contemplated, however.

For a multi-element sensor of a given configuration, the higher the value of the angle of deflection of the emitted beam, the greater the risk of appearance of what is called a "secondary lobe". This secondary lobe results from unwanted interference between beams of ultrasonic waves emitted respectively by different elemental transducers. This interference produces, besides the desirable, or primary, beam of ultrasonic waves, a secondary beam which is propagated in a direction generally opposite the direction of propagation of the primary beam. In general, such a phenomenon detracts from the effectiveness of the inspection. In particular, it may lead to a double detection of a flaw or even the generating of false alarms.

In practice, to prevent the appearance of a secondary lobe, the angle of refraction is limited to values compatible with a maximum value of the angle of deflection. This value, which is proper to each configuration of multi-element sensor, depends in particular on:
  the width of the elemental transducers (the narrower the elements, the higher the maximum value); and
  the wavelength in the coupling medium, that is, the speed of propagation of the ultrasonic waves in the medium and the frequency of excitation (the higher the frequency the lower the maximum value).

The configuration of its sensor allows the inspection device to implement variable values of the angle of refraction even to a value corresponding to the maximum value of the angle of deflection permitted by the sensor.

In the case when water is used as the coupling medium, and with a multi-element sensor of the type described in FIG. 5 used at a frequency of 5 megahertz, the maximum value of the angle of deflection below which the energy of the secondary lobes remains sufficiently restrained to not affect the quality of the inspection is around 15°. For a sensor having a radius of curvature of 40 millimeters, at a height of 14.5 millimeters of a pipe of 25.5 millimeters radius, this corresponds to a maximum value of the angle of incidence in water of around 24°, corresponding to an angle of refraction in transverse waves of 62.5°.

In practice, values of the angle of refraction between about 35° and about 60° are particularly suitable, which corresponds to values of incident angle in water between 15° and 23.5°.

Preferably, the proposed inspection device has a sensor which can be used at high frequency, on the order of 5 megahertz for example. Thus, the device is able to detect flaws of shallow depth.

The geometrical configuration of the sensor and its positioning with respect to the piece being inspected can be adapted so as to reduce the angle of divergence needed for given inspection conditions (angle of incidence and angle of refraction).

According to one particularly favorable configuration, the inspection device comprises a sensor of semi-encircling type, such as that shown in FIGS. 5 and 7 for example, whose curvature essentially corresponds to that of the piece being inspected. In this configuration, the ultrasound beams emitted by the subset are deflected in identical manner for the same angle of refraction.

Preferably, the active surface of the ultrasound translator is at a distance from the external surface of the piece being inspected which is large enough so that the imposed angle of deflection remains slight. This distance can correspond to the height of a water box, for example, the box 21 of FIG. 4. Preferably, this distance is greater than 10 millimeters.

Solely as an example, with a sensor of the type of FIG. 5, and for a pipe being inspected with an external diameter of 51 millimeters, with a distance between the active surface of the sensor and the external surface of this pipe of 14.5 millimeters, a value of the angle of deflection of 10.7° makes it possible to produce a beam having an angle of incidence of around 17° in the water. Under the same conditions, one needs an angle of deflection of around 14.1° at a distance of around 5 millimeters.

Reference is made to FIG. 13.

In response to the emitting of a beam of ultrasonic waves by a subset of elemental transducers, these elemental transducers can receive ultrasonic waves. These waves are converted into digital signals and recorded in the memory of the control electronics in relation to a time base.

The diagram of FIG. 13 shows one such signal. The amplitude of the signal received is shown along the ordinate, while the time base, corresponding to a flight time of the ultrasonic waves after their emission (reference origin) is shown along the abscissa.

The signal received has a first amplitude peak EC1, at a time t1, which corresponds to the reflection of a portion of the beam of ultrasonic waves incident on the surface of the tubular piece inspected. The peak EC1 can be called an "interface echo", since it results from the changing of medium between the coupling medium, which is located between the transducers and the piece, on the one hand, and the steel of this piece on the other hand. It corresponds to a portion of the energy diffused upon reflection of the beam incident on the external surface of the piece which returns to the sensor.

The time interval between the origin and the time t1 corresponds to the round trip flight time of the beam of ultrasonic waves in the coupling medium, between the multi-element sensor and the external surface of the piece.

The amplitude of the peak EC1 is rather slight, in particular more slight than the peak obtained in the classic inspection methods where the incident beam of ultrasonic waves propagates in a direction normal to the surface of the tubular piece inspected. This relative weakness of the amplitude of the peak EC1 results from the inclination of the incident beam with respect to this normal direction.

In the absence of flaws on the path of the beam of ultrasonic waves refracted in the inspected piece, the beam is reflected in the depth of the piece successively at the interface of the interior surface and air and at the interface of the exterior surface and coupling medium. In this case, no amplitude peak is visible any more in the A-scan after the first peak EC1.

Unlike the classical methods, where the incident beam propagates in the direction normal to the interface of the inspected piece, there is no amplitude peak here corresponding to the interface of the internal surface and air. This peak is sometimes called the "background echo" in the term of art.

In FIG. 13, a second amplitude peak EC2 occurs at time t2, which peak corresponds to the reflection of the refracted beam at a flaw. The gap between the times t2 and t1 corresponds essentially to a round trip flight time of the ultrasound waves between the external surface and the flaw. This time gap can be correlated with a depth value in the thickness of the tubular piece. This makes it possible to conclude here that the second peak EC2 results from a flaw located in proximity to the internal surface of the piece.

In the diagram of FIG. 13 there is shown by broken line a third amplitude peak EC3, at a time t3, which corresponds to the reception of a portion of the refracted beam reflected by a flaw located in the vicinity of the external surface of the tubular piece being inspected, after a rebound at its internal surface.

From the knowledge of the speed of propagation of the transverse ultrasonic waves in steel and the thickness of the tubular piece inspected, one can form a relation between the time base of the diagram of FIG. 13 and the depth in the thickness of the tubular piece.

One can advantageously define a first time slot F1, between times ti1 and tf1, which corresponds to a depth range of the flaws being searched for. The control electronics can comprise a system able to emit a warning signal when an amplitude peak greater than a threshold value AS1 is detected in the time slot F1.

In the same fashion, a second time slot F2 has been indicated, between times ti2 and tf2, corresponding to a zone near the external surface of the piece. The alarm system can be designed to emit a warning signal when an amplitude peak greater than a second threshold value AS2 occurs in the time slot F2.

Reference is made to FIG. 14.

This shows a diagram of A-scan type, such as can be put out by the control electronics, for example the electronics 100 of FIG. 6.

In principle, this A-scan diagram corresponds to the diagram of FIG. 13 except for the amplitude of the signal received, which is indicated here in a relative manner with respect to a screen height, calibrated for a minimum gain of a flaw being searched for, and the time base, which has been replaced by a datum of the distance traveled in the piece, deduced from the time base with the aid of a value for the speed of propagation in steel.

The A-scan of FIG. 14 also shows a first amplitude peak EC4 at a distance traveled of around 0 millimeters, corresponding to an interface echo, and a second amplitude peak EC5, with amplitude of around 80%, which occurs in the distance slot F4 and at a distance traveled of slightly less than 7 millimeters. The second peak EC5 corresponds for example to a flaw near the internal surface of the piece.

The boundaries of the distance slot F4 can be determined as a function of the thickness of the piece inspected. This makes it possible to locate a flaw in the thickness of the piece based on the position of the corresponding peak in the slot.

Reference is made to FIG. 15.

This shows a multi-element sensor 70 and a pipe 72 being inspected in a view similar to FIG. 7. The multi-element sensor 70 here is represented with a protection strip 75 for the elemental transducers, intercalated between the multi-element sensor 70 and the external surface 74 of the pipe 72.

According to one aspect of the invention, the control electronics comprises a controller, comprising for example the control circuit 110 and the processor 140 of the electronics 100 of FIG. 6, designed to apply successively a respective timed excitation law to subsets ETS1, . . . ETSN of elemental transducers mutually adjacent in the first direction. The successive excitation of each subset of transducers corresponds to what is known as an inspection sequence. After each application of a timed excitation law, the control electronics saves a digital representation, for example, in the form of a digital signal, of at least a portion of the electric signals resulting from the reception of ultrasound waves by the elemental transducers. Each time, the digital representations are saved in connection with an identification datum of the subset of elemental transducers to which the timed excitation law was applied.

Each timed excitation law defines a delay value for the respective emission of each elemental transducer of the corresponding subset.

In FIG. 15, as an example, there are represented seven subsets ETS1, . . . , ETS7 of sixteen elemental transducers each. Each time delay values respectively applied to the elemental transducers are represented in the form of a bar chart, each bar being associated with a respective elemental transducer and having a height proportional to the delay value applied to the transducer in question.

The timed excitation laws are such that the elemental transducers of the corresponding subset jointly produce a respective beam of ultrasound waves whose direction of propagation UB1, . . . , UB7 is inclined with respect to a direction normal to the external surface 74 of the pipe 72.

Here, each timed law is such that the beam of ultrasonic waves emitted is refracted at the external surface 74 of the pipe 72 into a respective beam of ultrasonic waves which propagates in a respective direction RB1, . . . , RB7 which is inclined with respect to the normal this external surface 74 by an angle between 35° and 60°, preferably near 40°.

In one embodiment, as illustrated in FIG. 15, the timed excitation laws are calculated such that the respective direction of propagation UB1, . . . , UB7 of each refracted beam has the same inclination or value of the angle of refraction with respect to a direction normal to the external surface 74.

Here, the shape correspondence between the surface of emission/reception of the sensor 70 and the exterior surface 74 of the pipe 72 makes it possible to apply essentially the same delay law to each subset of elemental transducers ETS1, . . . , ETS7.

Each inspection sequence produces the successive emission of beams which each encounter the exterior surface 74 of the pipe 72 at a respective place of incidence. Preferably, the places of incidence corresponding to an inspection sequence are regularly distributed over the angular portion which is inspected of the exterior surface 72.

The result is a sweeping of the transverse section of the pipe 72 over an angular portion thereof which exceeds the angular extent of the sensor 70 and/or that of a membrane such as the membrane 23 of FIG. 4. This sweeping takes place without movement of the sensor 70 relative to the pipe 72.

The subsets ETS1, . . . , ETS7 of elemental transducers are adjacent to each other in the first direction.

In FIG. 15, the subsets ETS1, . . . , ETS7 are moreover separate from each other: two consecutive subsets do not have any elemental transducer in common. The last elemental transducer of each subset is physically adjacent to the first elemental transducer of the next subset in the sequence. This corresponds to a simple embodiment of the invention, having the advantage among others of a rapid inspection sequence.

Advantageously, the controller is designed to successively excite the subsets having at least some elemental transducers in common. The result is a greater precision in the angular locating of the flaws, thanks to the places of incidence being closer to each other.

In general, the greater the number of elemental transducers in common to two successively excited subsets, the better the angular locating of the flaws (circumferential pointer). The sequence has a larger number of shots.

The subsets of elemental transducers which are controlled are determined in such a way that the gap between two adjacent places of incidence is small enough so that a flaw intercalated between these two places can be detected in an acceptable manner.

According to tests carried out by the applicant, a step of two elemental transducers (two consecutive subsets distinguish two elemental transducers from each other in the first direction) between two successive shots is sufficient. Such a step allows for the detecting of an internal flaw such as a longitudinal and radial nick with a depth of 0.5 millimeters in a pipe with outer diameter of 51 millimeters and thickness of 5 millimeters by using an ultrasound sensor of 5 megahertz. Each subset comprises 16 elemental transducers. For flaws positioned in intermediate manner, between two successive subsets, the response gap remains low, less than 1.5 dB, which confirms the homogeneity of the detection along the circumferential zone swept in this configuration.

Reference is made to FIG. 16.

This shows an image corresponding to what is known as a B scan diagram, such as may be produced by the output of the control electronics, such as the electronics 100 of FIG. 6.

The control electronics of the translator of the inspection device comprises a processing module designed to build up the A-scan recordings obtained for each subset of elemental transducers activated during the inspection sequence, or sweep.

On the abscissa is plotted the rank, in this sequence, of a respective subset. For example, the reference "11" here corresponds to the eleventh subset of elemental transducers activated.

Along the ordinate is plotted a common time base. For each rank value, the time origin corresponds to the excitation of the first elemental transducer of the subset, in relation to which the delay values applied to the other transducers of the subset are calculated.

For a given abscissa value, the trend of the diagram of FIG. 16 corresponds to an A-scan, for example, an A scan as described in regard to FIG. 14.

In the B-scan, the amplitude of the signals received can be represented by a color scale.

A B-scan diagram makes it possible to localize flaws in the thickness of the tubular piece inspected. A flaw can be localized not only in the depth of the thickness of the product, based on the flight time at maximum amplitude of the ultrasound echoes, but also in angular position by determining the rank of the subset of transducers corresponding to maximum amplitude. In other words, one can form a relation between a portion of the digital signals saved and the position data in the tubular piece, in the form of an identifier of a particular subset of elemental transducers. For example, the identifier in question comprises here an indication of the rank in the inspection sequence.

For example, FIG. 16 shows a flaw D1 in the angular position corresponding to that of the eleventh subset of elemental transducers.

As an option, a more precise position in the tubular piece can be recalculated by taking into account the angles of refraction of the ultrasound waves in the steel and their trajectory.

An inspection sequence can be carried out for each longitudinal position of the cart 7 with respect to the straight segment 3. The step between two longitudinal positions is synchronized with the time needed to perform an inspection sequence, generally less than one second.

The step may depend on the number of shots performed in a sequence, the frequency of repetition (PRF) of the electronics, and the desired inspection speed.

For example, with the microprocessors currently available, the applicant can obtain a speed of movement on the order of one meter per minute with a satisfactory axial point, typically on the order of a millimeter. By "axial pointer" is meant the distance between the places of incidence of beams of ultrasound waves of the same rank in two successive sequences, measured in the longitudinal direction of the piece, or the distance traveled by the cart between two successive sequences of shots.

Figure 17:
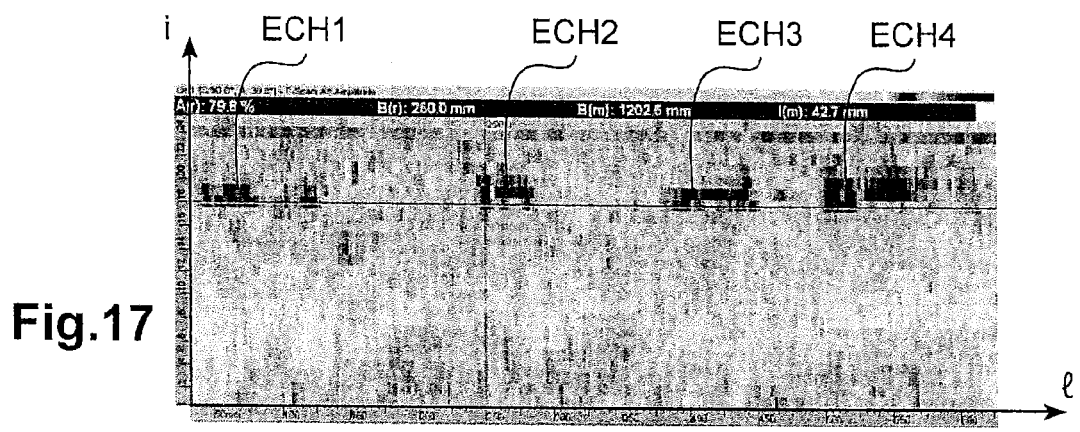
FIG. 17 represents a diagram of C-scan type as the result of a plurality of inspection sequences according to the first aspect of the invention.
Figure 18:
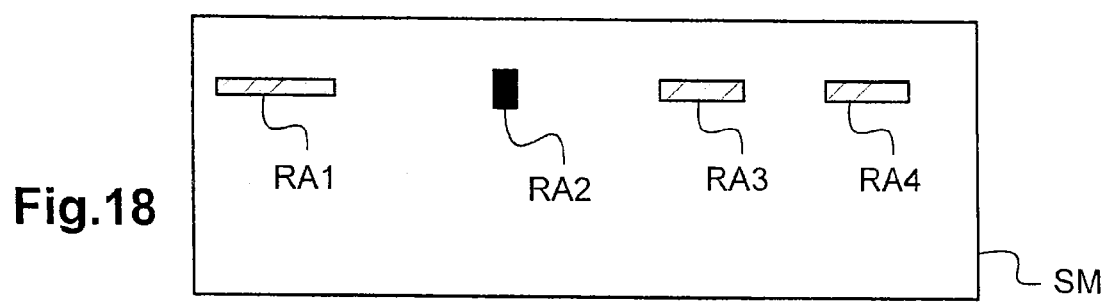
FIG. 18 represents a map of flaws corresponding to the diagram of FIG. 17.
Figure 19:
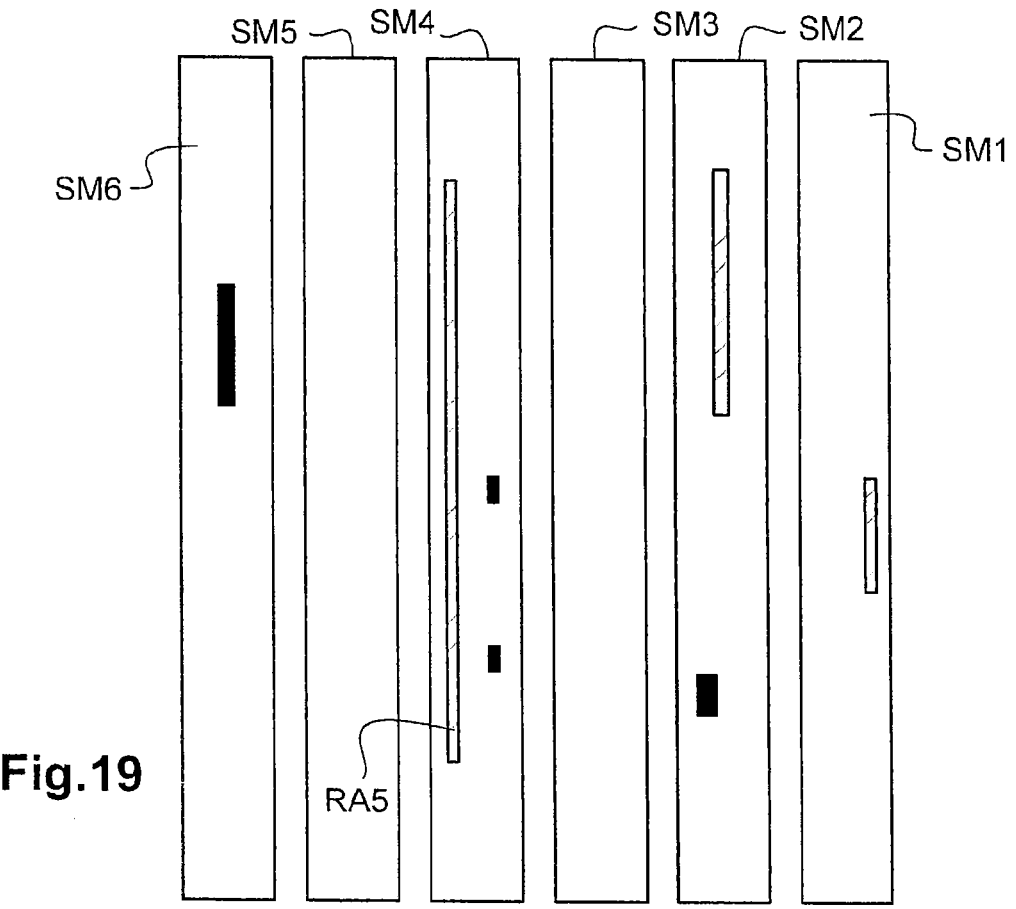
FIG. 19 represents a map of flaws of part of an installation based on tubular pieces.

Reference is made to FIGS. 17 to 19.

Advantageously, the control electronics is designed to utilize in addition the pulses of an encoder, such as the encoder 9 of FIG. 2, indicating a position of the multi-element sensor with respect to the length of the tubular piece, for each inspection sequence.

This makes it possible to construct a cartography of the piece, or a C-scan representation, as can be seen for example in FIG. 17.

On the abscissa is plotted the position 1 along the length of the piece to which the inspection sequence corresponds. This length can be obtained from the encoder. Along the ordinate is plotted the rank i of the subset used in the sequence. A position on the ordinate axis can be related to an angular position on the circumference of the zone inspected. The maximum amplitude of the ultrasound signal in a detection gate is represented by a color scale. Thus, a cartography can be recorded for each detection gate.

In FIG. 17, for example, the subsets of rank 18 and 19 "see" a first echo ECH1, corresponding to a first flaw, extending around 40 millimeters and 80 millimeters, a second echo ECH2 extending around 250 and 280 millimeters, a third echo ECH3 extending around 385 and 445 millimeters, and a fourth echo ECH4 extending between around 495 and 550 millimeters.

In an alternative representation, the flight time corresponding to the maximum amplitude of the ultrasound signal in the selected gate can be indicated also by a color scale.

The C-scans make it possible to localize any flaws along the longitudinal axis of the piece and estimate the extent of these flaws in this direction. The standardized method, known as the "method at −6 dB", consisting in estimating the length of a flaw by the distance where the amplitude of the signal remains greater than half (−6 dB) of the maximum amplitude obtained for this flaw, is particularly suitable for estimating the extent of flaws in the longitudinal direction of the piece, that is, the length of the flaw.

The greater the height of a flaw, that is, its dimension along the thickness of the tubular piece, the greater the amplitude of the beam reflected by this flaw. The inspection device can thus give an indication which can be taken into account to qualify the severity of the flaws detected.

To estimate the height of a radial flaw, one can compare the amplitude of the echoes received to the values obtained on similar pieces (similar dimensions and material) with artificial flaws, typically in the form of nicks of known depth. If the maximum amplitude value obtained for a natural flaw is within the observed amplitude values, for example, during a calibration phase, for two reference nicks with different depth from each other, then the natural flaw can be classified in a flaw range as defined by the height limits corresponding to the depth of the nicks.

A more precise estimation, particularly suitable when a linear relation is verified between the amplitude of the echoes and the height of the flaws, involves the preliminary calculation of a ratio between a maximum amplitude obtained for a reference nick and the depth of this nick, and then applying this ratio to the echoes obtained for the inspected piece.

Other approaches can be used, such as the joint use of the maximum amplitude of the echoes in the ultrasound signal and the width of the response of the flaw along the circumference of the product, or the number of groups where echoes corresponding to the flaw have been observed.

After this processing, a simplified cartography can be generated at the end of the inspection, such as can be seen in FIG. 18, for example. This cartography facilitates the quantitative interpretation of the results of the inspection for the users of the products.

Here, the simplified map SM comprises a rectangular zone corresponding to a longitudinal portion of an inspected piece, bounded in length and in circumference, on which the zones of the piece having flaws are represented in the form of zones of different colors. The color code can be representative of the class of severity of flaws detected in these zones. The dimensions and the position of the color zones correspond to the circumferential and axial positions as well as the length of the flaws detected.

The simplified map SM shows a rectangular zone RA1 whose extent along the length of the map SM corresponds to that of the first echo ECH1 of FIG. 17, and a second zone RA2, a third zone RA3 and a fourth zone RA4 corresponding respectively to the second, third and fourth echoes ECH2, ECH3, ECH4, respectively. The zones RA1, RA2, RA3 and RA4 are practically aligned with each other, which means that they correspond to flaws situated in the same angular sector of the inspected piece.

Again, in FIG. 18, the maximum amplitude of the signals received has been matched up with a gray tone value. The first zone RA1 and the fourth zone RA4 essentially show the same gray tone value. The corresponding flaws have heights close to one another, or at least belonging to the same range of height values. The second zone RA2 is darker than the first zone RA1. The flaw corresponding to the second zone RA2 has a greater height than that of the first zone RA1.

This can be realized, as shown by FIG. 19, for each of the tubular pieces of an installation, such as each of the segments 3 of FIG. 1. Each tubular piece corresponds to a simplified map SM1, . . . SMN.

In FIG. 19, the tubular pieces corresponding to the references SM5 and SM3 have no colored zones and can be considered as lacking any flaws, while the one referenced SM4 for example has a long colored zone RA5 corresponding to a flaw extending along the length of the corresponding tubular piece.

The resolution of the inspection along the longitudinal direction of the tubular piece, or axial pointer, can be defined as a function of the resolution of the desired cartography. Generally, it is less than the minimum length of the flaws which one wishes to detect.

The control electronics can calculate in real time the speed of advancement of the cart in relation to the tubular piece, in particular based on the pulses of the encoder. When the speed of advancement is too high in regard to the time needed to inspect a circumferential zone of the piece, a signal can be emitted for the inspection operator. The time needed to inspect a circumferential zone is essentially the same regardless of the longitudinal position of the cart with respect to the piece. It can be saved in the electronics after a first sequence of shots has been performed or calculated from inspection parameters, especially the number of shots performed in the course of this sequence. As an option, an excessively high speed of advancement can be indicated on the cartography by a "blank" in the acquisitions. This cartography is synchronized with respect to the length traveled thanks to the processing of the pulses of the encoder.

Figure 20:
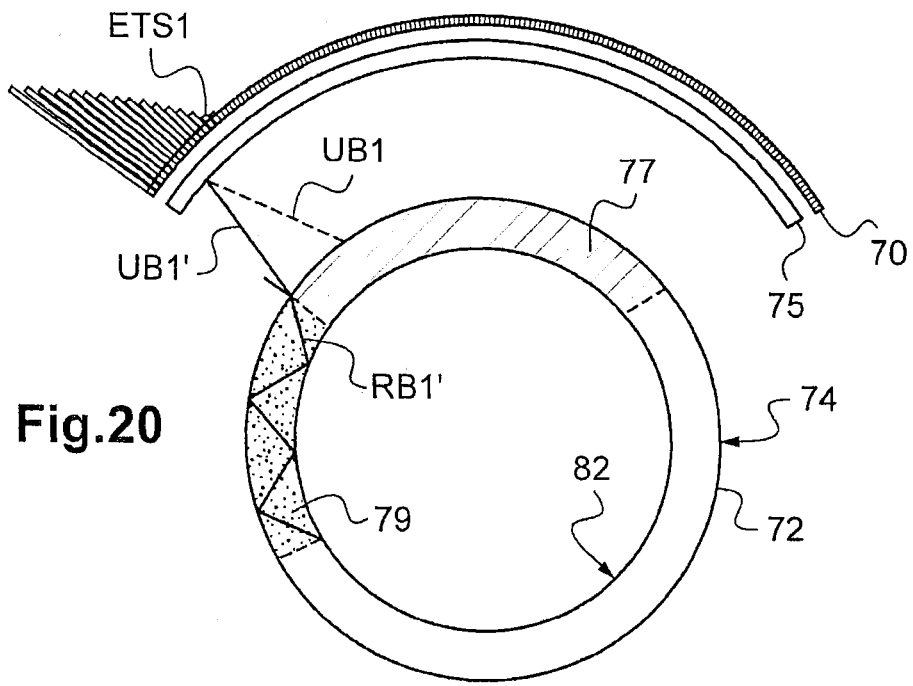
FIG. 20 represents an inspection round according to a second aspect of the invention.

Reference is made to FIG. 20.

This shows the sensor 70 and the pipe 72 being inspected in a relative position similar to that of FIG. 15.

The controller is designed to apply a timed excitation law such as a subset of elemental transducers located in the vicinity of one end of the sensor 70, here, the first subset ETS1 emits an incident ultrasound beam represented by its direction of propagation UB1'. The direction of propagation UB1' is opposite the normal (not shown) to the external surface 74 of the pipe 72 in the direction of propagation of the beam UB1 (shown by dotted line) at the place of incidence of the ultrasound beam.

The incident ultrasound beam propagating in the direction UB1' results in a refracted ultrasound beam which is propagated in the thickness of the pipe 72 along a direction RB1', and which moves away from the place of incidence, also moving away from a primary zone 77 of thickness of the pipe 72 corresponding to the projection of the sensor 70 onto the outer surface of the pipe 72. The pipe 72 can be inspected on an extended zone 79 (dotted line) greater than the zone 77 due to successive rebounds of the beam of ultrasonic waves refracted in the pipe 72, outside of the zone 77.

The extent of the zone of the pipe 72 which is actually inspected corresponds to the path of this beam in the thickness of the pipe 72. This dimension depends in particular on the number of rebounds of the beam refracted in the thickness of the pipe 72 and the thickness of the pipe 72. In practice, the refracted beam can rebound up to six times while maintaining a sufficient energy level to detect the presence of a flaw. This maximum number of rebounds can be influenced by the state of the internal and external surfaces of the pipe 72.

A round trip in the thickness of the pipe 72 can be called a "bounce". In FIG. 20, there is shown the refracted beam RB1' which rebounds 5 times on the external and internal surfaces, corresponding to 2.5 bounces.

For some of the subsets of elemental transducers, the inclination of the beam emitted can be modified so as to modify the inclination of the refracted beam in relation to the refracted beams resulting from incident beams emitted by the other subsets of the sequence. For example, the subsets corresponding to the elemental transducers situated at the lateral ends of the sensor can be controlled so that the refracted beam or beams have a greater inclination than the others, for example, between 50° and 60° instead of around 40°, and thus reach a broader inspection zone.

In the case of so-called "membrane tubes", that is, when the tubes are joined to each other by a flat fixed element, generally by a welding, on the length of two adjacent tubes, the increase in the inclination of the refracted beam may allow inspecting the zone of fixation of the element to the tube, or even the element itself, at least in part.

In one advantageous development, the controller is designed to control, in one inspection sequence, each subset of elemental transducers several times, according to different timed excitation laws with respect to each other, and designed to emit beams which are refracted with respective angles. This allows one, for example, to detect flaws which are slightly inclined with respect to the radial direction of the piece. In particular, each inspection sequence can call for each subset of elemental transducers emitting two incident beams, opposite each other. Each flaw present in the primary inspection zone can then be seen along two mutually opposite faces. The result is a more reliable inspection, especially in the case of asymmetrical flaws.

Figure 21:
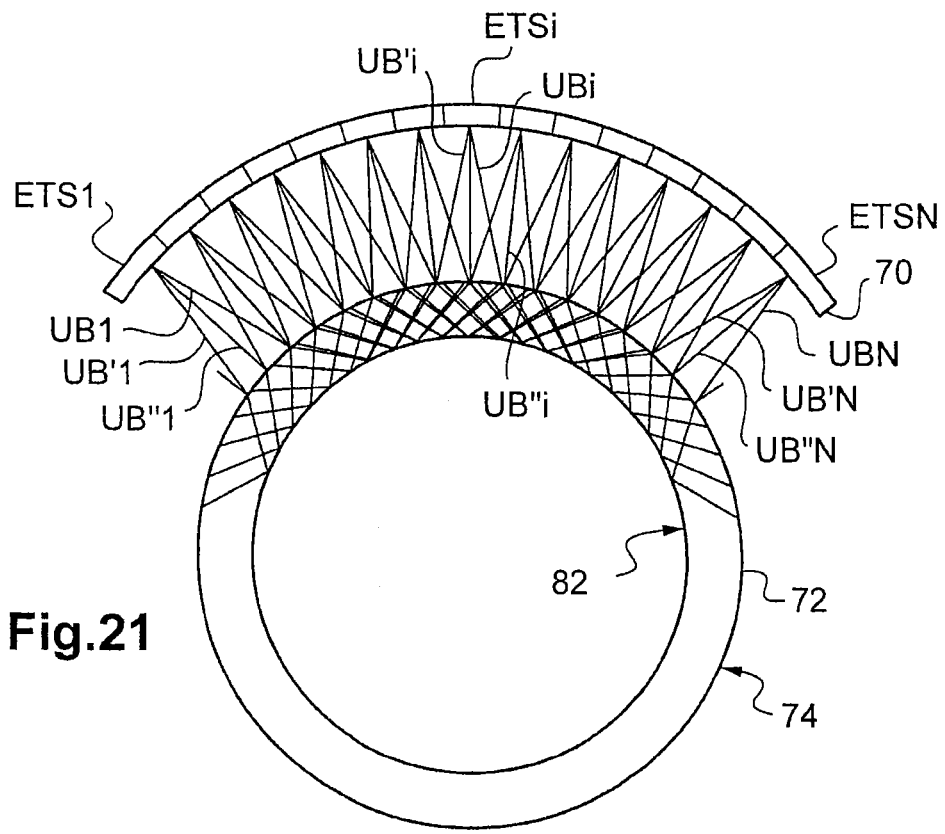
FIG. 21 represents an inspection sequence according to a third aspect of the invention.

Reference is made to FIG. 21.

Each subset ETSi of the sensor 70 emits during an inspection sequence:
  a first beam of ultrasonic waves UBi on one side from the direction normal to the external surface of the piece inspected, in a manner analogous to FIG. 15;
  a second beam of ultrasonic waves UB'i inclined by the same angle on the other side of this normal direction;
  a third incident beam of ultrasonic waves UB"i propagating along this normal direction The group of shots of ultrasonic waves with opposite directions in relation to the direction normal to the surface of the piece being inspected makes it possible to obtain a reflected beam for each of the faces of an essentially radial flaw of the primary inspection zone, which improves the detection and the qualification of the flaw.

Each shot in the normal direction (UB"i) allows one to determine a thickness value of the piece where the beam penetrates the piece, among other things.

A cross interpretation (or data merging) between the obtained cartographies and the thickness cartographies lets one estimate the residual thickness of the piece where flaws have been detected. This information can assist in estimating the remaining service life of the piece.

In a zone having a flaw, one matches up a relative thickness value for this zone (the measurement of thickness per straight shot is not affected by the presence of a radial crack type flaw) with an estimated height value for the flaw in question. The subtraction of these values can be used as an estimate of a residual thickness value, that is, the thickness of sound material remaining in the zone.

The user can then compare this value to a minimum value, for example, one obtained from a structural calculation, and estimate the remaining service life of the piece and/or decide on its replacement.

Moreover, straight shots in addition to inclined shots make it possible to ensure the quality of the coupling between the sensor and the external surface of the piece: as long as the amplitude of the background echoes is greater than a threshold value, such as one defined by the inspector and/or the inspection procedure, the coupling can be considered to be effective.

Figure 22:
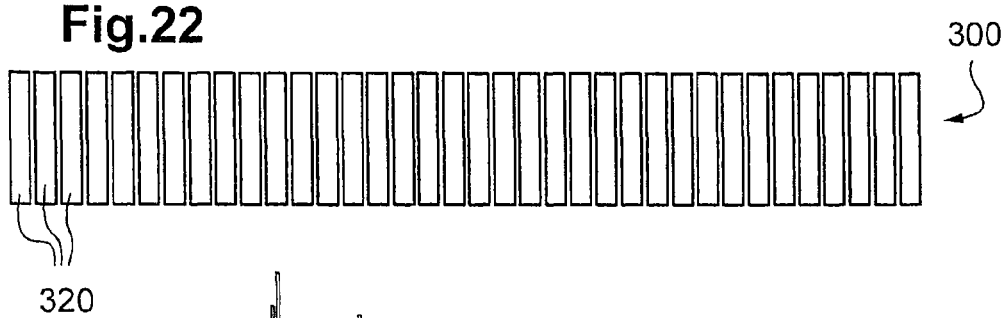
FIG. 22 represents a multi-element sensor as a variant of the sensor of FIG. 5.

Reference is made to FIG. 22.

This shows one variant of a multi-element sensor, for example, to be used as a surface of emission/reception 19 of FIG. 4, in the form of a flat sensor 300.

The flat sensor 300 contains a plurality of ultrasound transducers 320 which are similar to each other and distributed on a line on a generally flat surface. The ultrasound transducers 320 are for example analogous to the elemental transducers 32 described in connection with FIG. 5.

In one variant not shown, the surface of emission/reception can generally be curved and/or not concentric with the external surface profile of the piece being inspected. In general, the shape of this surface of emission/reception can differ from that of the external surface of the piece being inspected, in particular, for reasons of footprint or available sensor shape. The calculation of the laws of delay to be applied should then be modified as a consequence.

A flat sensor, such as the sensor 300, can have a more practical footprint than a curved sensor, for example when the tubular pieces are in mutual contact by means of their respective external surface.

Figure 23:
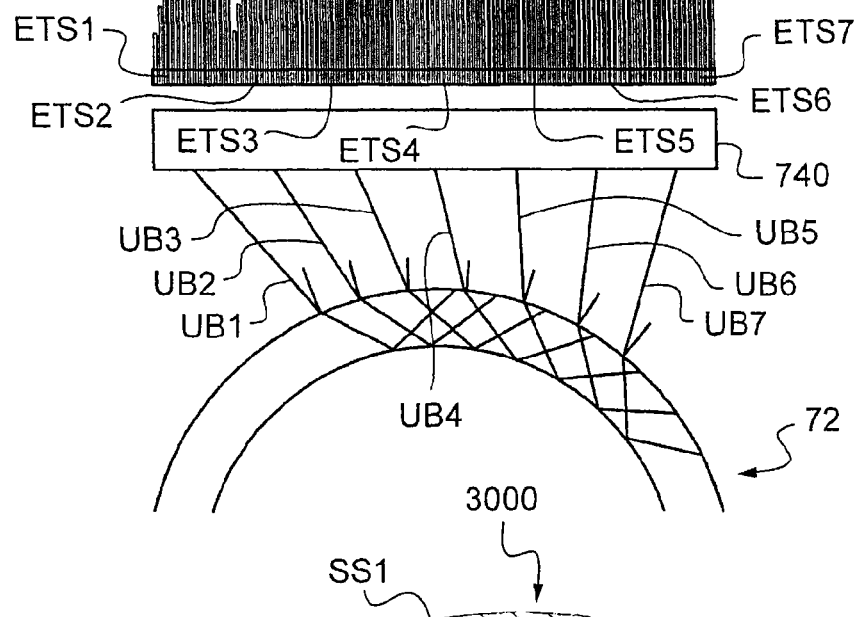
FIG. 23 shows an inspection sequence as a variant of the sequence of FIG. 15.

Reference is made to FIG. 23.

This shows a variant of a multi-element sensor in the form of a flat sensor 700, in position with respect to the pipe being inspected 72. The flat sensor 700 is illustrated with a protection strip 740

Opposite each subset of elemental transducer ETSi are shown the delays to be applied to each elemental transducer so that the subset in question emits a beam of ultrasonic waves UBi which is inclined by a given angle of incidence with respect to the direction normal to the external surface of the pipe 72 at the place of incidence.

Unlike the semi-encircling translator described above, the laws of delay to be applied to each subset ETSi are different from each other.

The use of a flat sensor such as the sensor 700 means different laws of delay with respect to each other and a smaller inspected zone for a footprint in the first direction of the comparable sensor. The sensor 700, however, can be used advantageously in certain particular instances, especially for lack of sufficient space to place a semi-encircling sensor on the installation being inspected.

Figure 24:
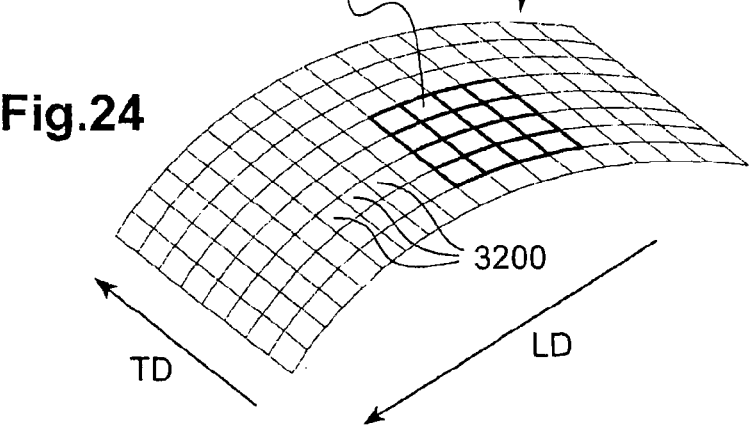
FIG. 24 represents a multi-element sensor as yet another variant of the sensor of FIG. 5.

Reference is made to FIG. 24.

This shows yet another variant of a multi-element sensor for use as a surface of emission/reception 19 of FIG. 4, in the form of a two-dimensional sensor 3000.

The two-dimensional sensor 3000 comprises a plurality of elemental transducers 3200 distributed in a two-dimensional pattern, here, over a curved surface. The pattern here is in the form of a table extending in two directions LD and TD perpendicular to each other, one of them, such as the direction LD, corresponding to the first direction of the translator. As a variant, the surface on which the elemental transducers 3200 are distributed can be planar.

The two-dimensional sensor 3000 allows a checking of a tubular piece in a single pass with regard to the existence of longitudinal flaws, like the one-dimensional sensors described above, and transverse flaws and/or oblique flaws. For the detection of longitudinal flaws, the process of emission/reception is analogous to that described above.

For the inspection for transverse flaws, the controller causes beams of ultrasound waves to be emitted, which propagate in an inclined direction with respect to the longitudinal axis of the pipe being inspected and contained within a plane containing this longitudinal axis. One uses laws of delay which are applied successively to subsets comprised of elemental transducers aligned in a direction parallel to the longitudinal axis of the pipe being inspected, here, the direction TD.

For the inspection for oblique flaws, corresponding laws of delay can be applied to subsets comprised of elemental transducers belonging to rows and columns of the two-dimensional sensor 3000. In other words, one uses subsets of elemental transducers which are mutually adjacent in the direction TD furthermore comprising elemental transducers which are mutually adjacent in the direction LD. For example, the subset SS1 of FIG. 24 corresponds to a square pattern of four elements on each side.

Timed excitation laws can be designed so that the elemental transducers of the respective subset jointly produce an incident beam of ultrasonic waves furthermore inclined with respect to the longitudinal direction of the tubular piece and/or the transverse direction of this piece. In other words, the beam of ultrasonic waves in question propagates in a direction which, projected onto a transverse plane of this piece, is inclined with respect to the transverse direction, and/or projected onto a plane passing through the longitudinal axis of the piece, is inclined with respect to the longitudinal direction of the piece.

We have been describing an inspection device suitable for the inspection of tubular pieces, such as the segments 3, on a portion of their circumference close to a half-circumference. Depending on the applications, the portion inspected can be more extensive, in particular if it is possible to increase the angular dimension of the emitting surface of the translator 17, taking into account the configuration of the installation being inspected and especially the gap between two adjacent segments.

The proposed device is particularly suitable for the inspection of tubular pieces where a circumferential zone equal to or less than the half-circumference is more particularly stressed during operation. For example, in the case of an installation designed for heat exchange, only one part of the circumference of the piece is exposed to the heat source. The portion of the piece oriented toward this source is primarily stressed. The inspection can be limited to a zone less than or equal to the corresponding half-circumference.

As a variant, it is possible to make two inspection passes, each pass corresponding each time to one side of a panel, and more generally as many passes as are needed to cover the circumferential zone being inspected.

The proposed device is particularly suited to the inspection of tubular pieces in installations where a dismantling of these pieces is not feasible. It is also particularly advantageous in the case when the tubular piece being inspected is in a cluttered zone or when the piece, or the structure in which it is mounted, has a complex geometry. Thanks to this, the proposed device is very useful in the case of inspection on site. It can also be used advantageously at the production site of the tubular piece, especially whenever an automatic inspection bench cannot be used.

The different shots of ultrasound waves are done consecutively, one group of elements at a time, during circumferential sweeps. Thus, the different inspections are done in a single translatory pass over the piece.

The above-described inspection device is fundamentally distinguished from known devices in that it generates one or more incident beams of ultrasonic waves, each one inclined with respect to a direction normal to the external surface of the piece being inspected at the place of incidence.

An incident beam propagating normally to this external surface results in a received signal comprising two echoes relative to the geometry of the piece inspected: a first or interface echo, corresponding to the interface between the coupling medium and the piece, at the external surface of the piece, and a second or background echo, corresponding to the interface between the piece and the air, at the internal surface of the piece. If a flaw is present in the thickness of the piece, with an orientation principally perpendicular to the ultrasound beam, i.e., tangential or transverse, then a supplemental echo will appear.

If this flaw is close to the external surface or the internal surface of the piece, then the echo received in response might be confused with the interface echo or the background echo, respectively. And this flaw cannot be easily detected. In the classical art, the corresponding zones are sometimes called "blind zones" due to this fact.

Moreover, a refracted ultrasound beam which propagates radially in the tubular piece is not favorable to a reflection at radial cracks of slight width, such as is the case typically with fatigue or corrosion cracks.

The described device is particularly suitable for inspection of rectilinear segments of tubular pieces. It can also be used for the inspection of curved zones, for example, the elbows 5 of FIG. 1. The encoding of the position might have to be adapted.

The invention is not limited to the embodiments described above, solely as examples, but also encompasses all the variants which may be contemplated by the skilled person.

For example, we have primarily described the use of water as a coupling medium. Other types of medium can be used. Each time one should determine the values of the angle of incidence corresponding to this medium, as a function of the speed of sound of the longitudinal waves in the particular coupling medium in order to reach the desired angles of refraction. One can make use of the formula of Annex A.2 for example. Thus, we have described a value for the angle of incidence of 17° in water, corresponding to a preferred value of the angle of refraction of 40° in steel. This preferred value of the angle of refraction in steel corresponds to an angle of incidence of around 18.5° in Aqualene and around 32° in plexiglas.

In similar fashion, the preferred value of the angle of refraction of 40° in steel can be modified for tubular pieces made of different materials, still making use of the formula of Annex A.2 for example.

The described device can include several carts of the type described in FIGS. 2 to 4, connected to the same electronics in order to improve the inspection cadence. In certain configurations, the different carts can execute different control laws for the elemental transducers. Under certain conditions, the different carts can be outfitted with sensors of different configuration.

Annex A: mathematical formulas $$\Delta t_n = \frac{d_n}{V}\sin(\beta) \qquad \text{Annex A.1}$$

-continued $$\frac{\sin(\theta 1)}{V1_L} = \frac{\sin(\theta 2_L)}{V2_L} = \frac{\sin(\theta 2_T)}{V2_T} \qquad \text{Annex A.2}$$

$$\cos(\beta) = \frac{D - r_1 \cdot \sqrt{D} \cdot \cos(\theta)}{r_2 \cdot (\sqrt{D} - r_1 \cdot \cos(\theta))} \qquad \text{Annex A.3}$$

$$D = r_1^2 \cdot (\cos^2(\theta) - 1) + r_2^2 \qquad \text{Annex A.4}$$

The invention claimed is:

1. A device for inspection of tubular pieces, comprising:
   at least one cart including:
      a plurality of elemental transducers of electroacoustic type, distributed along at least a first direction; and
      a guide configured to cooperate with an exterior surface of a tubular piece being inspected to position the cart such that the first direction essentially corresponds to a direction transverse to the tubular piece;
   a control electronics, connected to the electroacoustic transducers;
   wherein the control electronics comprises:
      a memory storing one or more timed excitation laws;
      one or more controllers configured to apply in succession at least one respective timed excitation law to subsets of mutually adjacent elemental transducers along the first direction; and
   wherein at least certain of the timed excitation laws are designed so that the elemental transducers of the respective subsets jointly produce incident beams of ultrasonic waves propagating along respective directions inclined relative to a direction normal to the exterior surface of the tubular piece.

2. A device according to claim 1, wherein at least certain of the timed excitation laws are designed so that the elemental transducers of the respective subsets produce incident beams of ultrasonic waves propagating along respective directions having the same inclination with respect to the direction normal to the exterior surface of the tubular piece.

3. A device according to claim 1, wherein at least certain of the timed excitation laws are designed so that the elemental transducers of the respective subsets produce incident beams of ultrasonic waves which are refracted at least partly in the tubular piece into beams of ultrasonic waves propagating along respective directions, each one having an inclination greater than around 35° with respect to the direction normal to the exterior surface of the tubular piece.

4. A device according to claim 1, wherein at least certain of the timed excitation laws are designed so that the elemental transducers of the respective subsets produce incident beams of ultrasonic waves which are refracted at least partly in the tubular piece into beams of ultrasonic waves propagating along respective directions, each one having an inclination less than around 60° with respect to the direction normal to the exterior surface of the tubular piece.

5. A device according to claim 1, wherein at least certain of the timed excitation laws are designed so that the elemental transducers of the respective subsets produce incident beams of ultrasonic waves which are refracted at least partly in the tubular piece into beams of ultrasonic waves propagating along respective directions, each one having an inclination near around 40° with respect to the direction normal to the exterior surface of the tubular piece.

6. A device according to claim 1, wherein each controller is configured to apply plural respective timed excitation laws to at least certain of the subsets of elemental transducers, the respective timed excitation laws of the subsets of elemental transducers being designed to produce incident beams of ultrasonic waves propagating along respective directions, each one inclined by the same angle on either side of a direction normal to the exterior surface of the tubular piece.

7. A device according to claim 1, wherein each controller is configured to apply plural respective timed excitation laws to at least certain of the subsets of elemental transducers, at least one of the respective timed excitation laws of each subset being designed to produce an incident beam of ultrasonic waves propagating along a direction normal to the exterior surface of the tubular piece.

8. A device according to claim 1, wherein the control electronics is configured to save digital representations of at least a portion of electric signals resulting from a reception of ultrasonic waves by at least some of the elemental transducers after each application of a timed excitation law to a respective subset of elemental transducers, and the digital representations are saved in connection with an identifier of the respective subset of elemental transducers.

9. A device according to claim 8, wherein the control electronics further comprises at least one processing module configured to operate on at least some of the digital representations, and wherein the processing module is configured to operate each time on the digital representations saved in connection with the same identifier of the subset of elemental transducers.

10. A device according to claim 9, wherein the processing module is configured to operate each time only on the digital representations of electric signals resulting from a reception of ultrasonic waves by the elemental transducers of the subset to which the timed excitation law was applied, or at least some of them.

11. A device according to claim 9, wherein the processing module is configured to establish a correspondence between a part of at least one of the digital representations and an angular position datum in the tubular piece and/or a position datum in the thickness of the piece.

12. A device according to claim 11, wherein the angular position datum comprises an identifier of a particular elemental transducer and/or of a particular subset of elemental transducers.

13. A device according to claim 12, wherein the particular elemental transducer and/or the particular subset of elemental transducers are selected based on a maximum amplitude value among the digital representations associated with different identifiers of subsets of elemental transducers.

14. A device according to claim 8, wherein a processing module is configured to establish a relation between amplitude data in the digital representations and longitudinal position data and/or transverse position data with respect to the piece inspected.

15. A device according to claim 14, wherein at least some of the amplitude data results from a comparison of at least some of the digital representations at one or more threshold values.

16. A device according to claim 1, wherein at least two subsets excited successively have one or more elemental transducers in common.

17. A device according to claim 1, further comprising one or more ultrasound coupling elements integrated with the cart, and intercalated between the plurality of elemental transducers and the tubular piece.

18. A device according to claim 1, further comprising a position encoder attached to the cart and connected to the control electronics, wherein the control electronics is configured to save a digital representation of at least a portion of electric signals resulting from a reception of ultrasonic waves by at least some of the elemental transducers after each application of a timed excitation law to a respective subset of elemental transducers, and the digital representations are saved in connection with a position datum with regard to the tubular piece resulting from the position encoder.

19. A device according to claim 1, wherein the cart comprises an active surface corresponding in shape to the tubular piece, and the elemental transducers are distributed over the active surface.

20. A device according to claim 1, wherein the elemental transducers are distributed along at least one second direction, and the guide is configured to cooperate with the exterior surface of the tubular piece being inspected to position the cart such that the second direction corresponds essentially to a longitudinal direction of the tubular piece.

21. A device according to claim 20, wherein at least some of the subsets of elemental transducers which are mutually adjacent along the first direction further include elemental transducers which are mutually adjacent along the second direction, and at least some of the timed excitation laws are designed so that the elemental transducers of the respective subset jointly produce an incident beam of ultrasonic waves propagating along a direction inclined further in relation to the longitudinal direction of the tubular piece and/or a transverse direction of the piece.

22. A device according to claim 1, wherein the controller is configured to apply a respective timed excitation law to a subset at least of elemental transducers close to one end of the distribution of elemental transducers, the timed excitation law being designed so that the elemental transducers of at least one of the subsets near one end of the cart jointly produce an incident beam of ultrasonic waves propagating along a direction more inclined with respect to a direction normal to the outer surface of the tubular piece than the rest of the subsets.

23. A method for inspection of tubular pieces, in which a guide cooperates with an exterior surface of a tubular piece being inspected to position at least one cart including a plurality of elemental transducers of electroacoustic type such that the transducers are distributed along at least one transverse direction of the tubular piece, comprising:
  at least one inspection including a consecutive application of at least one timed excitation law to subsets of mutually adjacent elemental transducers along a first direction so that the elemental transducers of each respective subset jointly produce an incident beam of ultrasonic waves propagating along a direction inclined with respect to a direction normal to the exterior surface of the tubular piece.

24. A method for inspection of tubular pieces according to claim 23, wherein the cart is displaced along the length of the tubular piece being inspected after each inspection.

* * * * *

UNITED STATES PATENT AND TRADEMARK OFFICE
CERTIFICATE OF CORRECTION

PATENT NO. : 9,810,666 B2  
APPLICATION NO. : 14/773634  
DATED : November 7, 2017  
INVENTOR(S) : Francois Deneuville Page 1 of 1

It is certified that error appears in the above-identified patent and that said Letters Patent is hereby corrected as shown below:

In the Specification

Column 11, Line 8, change "interface IVF between" to --interface INTF between--; and Column 11, Line 22, change "interface IVF into" to --interface INTF into--.

Signed and Sealed this
Fifth Day of March, 2019

Andrei Iancu
*Director of the United States Patent and Trademark Office*